US00RE46504E

(19) United States
(12) Reissued Patent
Dahm et al.

(10) Patent Number: US RE46,504 E
(45) Date of Reissued Patent: Aug. 8, 2017

(54) LIGHT DELIVERY SYSTEM

(71) Applicant: PURDUE PHARMACEUTICAL PRODUCTS L.P., Stamford, CT (US)

(72) Inventors: Jonathan S. Dahm, Key Largo, FL (US); William Louis Barnard, Maple Valley, WA (US); James C. Chen, Clyde Hill, WA (US); David B. Shine, Littleton, CO (US)

(73) Assignee: PURDUE PHARMACEUTICAL PRODUCTS L.P., Stamford, CT (US)

(21) Appl. No.: 15/088,702

(22) Filed: Apr. 1, 2016

Related U.S. Patent Documents

Reissue of:
(64) Patent No.: 8,685,005
Issued: Apr. 1, 2014
Appl. No.: 12/445,061
PCT Filed: Oct. 11, 2007
PCT No.: PCT/US2007/081131
§ 371 (c)(1),
(2) Date: Feb. 5, 2010
PCT Pub. No.: WO2008/046015
PCT Pub. Date: Apr. 17, 2008

U.S. Applications:
(60) Provisional application No. 60/851,141, filed on Oct. 11, 2006.

(51) Int. Cl.
*A61B 18/18* (2006.01)
*A61N 5/06* (2006.01)
(Continued)

(52) U.S. Cl.
CPC ..... *A61N 5/062* (2013.01); *A61N 5/0601* (2013.01); *A61B 18/24* (2013.01); *A61N 2005/0652* (2013.01)

(58) Field of Classification Search
CPC ..... A61N 5/062; A61N 2005/0652
(Continued)

(56) References Cited

U.S. PATENT DOCUMENTS 4,445,892 A 5/1984 Hussein et al.
4,470,407 A 9/1984 Hussein
(Continued)

FOREIGN PATENT DOCUMENTS

EP 0266038 A2 5/1988
EP 0755697 A2 1/1997
(Continued)

OTHER PUBLICATIONS

Jonathan S. Dahm, "Flexible Intra-Body Photo-Therapy Device Containing Transparent Substrate LED's on a Transparent Polymetric Substrate," U.S. Appl. No. 60/581,167, filed Jun. 17, 2004, 7 pages.

(Continued)

*Primary Examiner* — Cary Wehner
(74) *Attorney, Agent, or Firm* — Troutman Sanders LLP

(57) ABSTRACT

A light delivery system to provide light treatment to a patient includes a catheter assembly having a plurality of light sources that transmit light towards a target site within a patient. In one embodiment, the light delivery system has a plurality of light sources mounted to a flexible transparent base that extends at least partially through a distal tip of the catheter assembly. The light sources can be wire bonded or mounted in a flip chip arrangement onto the base. In one embodiment to produce the distal tip, an array of light energy sources can be held by an array of holders of a fixture device. A vacuum is applied to secure each light energy source in a corresponding holder. While the vacuum is applied, the energy sources are electrically connected by wire bonding. The vacuum can be reduced or stopped thereby permitting removal of the light energy sources from the fixture device.

45 Claims, 21 Drawing Sheets

(51) Int. Cl.

| | |
|---|---|
| ***A61B 19/00*** | (2006.01) |
| ***A61N 1/30*** | (2006.01) |
| *A61B 18/24* | (2006.01) |

(58) Field of Classification Search

USPC ..... 606/2–19; 604/4, 21; 600/156–183; 607/88–94; 128/898

See application file for complete search history.

(56) References Cited

U.S. PATENT DOCUMENTS

| | | | | |
|---|---|---|---|---|
| 4,558,690 | A | 12/1985 | Joyce | |
| 4,822,335 | A | 4/1989 | Kawai et al. | |
| 4,886,831 | A | 12/1989 | Morcos et al. | |
| 4,932,934 | A | 6/1990 | Dougherty et al. | |
| 4,957,481 | A | 9/1990 | Gatenby | |
| 5,071,407 | A | 12/1991 | Termin et al. | |
| 5,104,392 | A | 4/1992 | Kittrell et al. | |
| 5,129,889 | A | 7/1992 | Hahn et al. | |
| 5,132,101 | A | 7/1992 | Vogel et al. | |
| 5,146,917 | A | 9/1992 | Wagnieres et al. | |
| 5,163,898 | A | 11/1992 | Morcos et al. | |
| 5,298,018 | A | 3/1994 | Narciso, Jr. | |
| 5,330,465 | A | 7/1994 | Doiron et al. | |
| 5,370,608 | A | 12/1994 | Sahota et al. | |
| 5,445,608 | A * | 8/1995 | Chen et al. | 604/20 |
| 5,609,591 | A | 3/1997 | Daikuzono | |
| 5,662,712 | A | 9/1997 | Pathak et al. | |
| 5,766,234 | A | 6/1998 | Chen et al. | |
| 5,779,697 | A | 7/1998 | Glowa et al. | |
| 5,782,896 | A | 7/1998 | Chen et al. | |
| 5,800,478 | A | 9/1998 | Chen et al. | |
| 5,814,008 | A | 9/1998 | Chen et al. | |
| 5,827,186 | A * | 10/1998 | Chen | A61N 5/0601 600/407 |
| 5,830,210 | A | 11/1998 | Rudko et al. | |
| 5,865,840 | A * | 2/1999 | Chen | A61N 5/062 604/500 |
| 5,876,427 | A * | 3/1999 | Chen | A61N 5/0601 257/E25.021 |
| 5,941,626 | A | 8/1999 | Yamuro | |
| 5,947,958 | A | 9/1999 | Woodard et al. | |
| 5,957,960 | A * | 9/1999 | Chen | A61K 41/008 607/88 |
| 5,997,571 | A | 12/1999 | Farr et al. | |
| 6,058,323 | A | 5/2000 | Lemelson | |
| 6,086,558 | A | 7/2000 | Bower et al. | |
| 6,171,299 | B1 | 1/2001 | Bonutti | |
| 6,231,568 | B1 | 5/2001 | Loeb et al. | |
| 6,245,012 | B1 | 6/2001 | Kleshinski | |
| 6,336,934 | B1 | 1/2002 | Gilson et al. | |
| 6,355,030 | B1 | 3/2002 | Aldrich et al. | |
| 6,445,011 | B1 | 9/2002 | Hirano et al. | |
| 6,485,502 | B2 | 11/2002 | Don Michael et al. | |
| 6,540,767 | B1 | 4/2003 | Walak et al. | |
| 6,562,058 | B2 | 5/2003 | Seguin et al. | |
| 6,575,965 | B1 | 6/2003 | Fitch et al. | |
| 6,585,655 | B2 | 7/2003 | Crowley | |
| 6,661,167 | B2 | 12/2003 | Eliashevich et al. | |
| 6,749,623 | B1 | 6/2004 | Hsi et al. | |
| 6,784,460 | B2 | 8/2004 | Ng et al. | |
| 6,811,562 | B1 | 11/2004 | Pless | |
| 6,830,584 | B1 | 12/2004 | Seguin | |
| 6,953,457 | B2 | 10/2005 | Farr et al. | |
| 6,958,498 | B2 | 10/2005 | Shelton et al. | |
| 7,135,034 | B2 | 11/2006 | Friedman et al. | |
| 7,261,730 | B2 | 8/2007 | Friedman et al. | |
| 2004/0230156 | A1 | 11/2004 | Schreck et al. | |
| 2005/0085455 | A1 | 4/2005 | Chen | |
| 2005/0104059 | A1 * | 5/2005 | Friedman | A61M 25/1011 257/40 |
| 2005/0228260 | A1 | 10/2005 | Burwell et al. | A61N 5/0601 600/408 |
| 2008/0027517 | A1 * | 1/2008 | Burwell et al. | 607/88 |
| 2008/0281305 | A1 * | 11/2008 | Baynham | A61F 2/82 606/10 |
| 2012/0149986 | A1 * | 6/2012 | Burwell | A61N 5/062 600/178 |

FOREIGN PATENT DOCUMENTS

| | | | |
|---|---|---|---|
| JP | 08-505803 | | 6/1996 |
| JP | 11-186590 | | 7/1999 |
| JP | 11-242451 | | 9/1999 |
| JP | 2002-222998 | | 8/2002 |
| JP | 2005-129821 | | 5/2005 |
| WO | WO-9505214 | | 2/1995 |
| WO | 9743965 | A1 | 11/1997 |
| WO | 0207629 | A1 | 1/2002 |
| WO | 0241364 | A2 | 5/2002 |
| WO | 2004082736 | A2 | 9/2004 |
| WO | 2006031934 | A2 | 5/2006 |
| WO | WO-2008046015 | | 4/2008 |

OTHER PUBLICATIONS

Phillip Burwell, "Flexible LED Arrays for Phototherapeutic Procedures," U.S. Appl. No. 60/640,382, filed Dec. 30, 2004, 13 pages.

PCT International Search Report, mailed Mar. 19, 2008, for PCT/US2007/081131, 13 pages.

Japan Patent Office, Official Office Action, counterpart JP Patent Application 2009-532583, mailed Sep. 5, 2012, 12 pages (includes English Translation).

International Searching Authority, Written Opinion, PCT Application PCT/US2007/081131, Apr. 11, 2009, 6 pages.

Noguchi, H., "The Photodynamic Action of Eosin and Erythrosin upon Snake Venom," *Journal of Experimental Medicine,* 1906, vol. 8, pp. 252-266.

Bolande et al., "Photodynamic Action," *Archives of Pathology,* 1963, vol. 75, pp. 115-122.

Ballio et al., "Research Progress in Organic-Biological and Medicinal Chemistry," *Societa Editoriale Farmaceutica,* 1964, vol. I, pp. 260-336.

Tapper et al., "Photosensitivity from Chlorophyll-Derived Pigments," *Journal of the Science of Food and Agriculture,* 1975, vol. 26, pp. 277-284.

Ison et al., "Phototoxicity of Quinoline Methanols and Other Drugs in Mice and Yeast," *The Jounral of Investigative Dermatology,* 1969, vol. 52, No. 2, pp. 193-198.

Eskins et al., "Sensitized Photodegradation of Cellulose and Cellulosic Wastes," *Photochemistry and Photobiology,* 1973, vol. 18, pp. 195-200.

Krinsky, N., "Cellular Damage Initiated by Visible Light," *Symposia of Society for General Microbiology,* 1976, pp. 209-239.

Song et al., "Photochemistry and Photobiology of Psoralens," *Photochemistry and Photobiology,* 1979, vol. 29, pp. 1177-1197.

Haas et al., "Photodynamic Effects of Dyes on Bacteria," *Mutation Research,* 1979, vol. 60, pp. 1-11.

Webb et al., "Photodynamic Effects of Dyes on Bacteria," *Mutation Research,* 1979, vol. 59, pp. 1-13.

Barltrop et al., "Potential Management of Florida Red Tide Through Selective Photodynamic Action," *Journal of Environmental Science and Health,* 1980, AI5(2), pp. 163-171.

Parrish, J., "Photobiologic Considerations in Photoradiation Therapy," *Proceedings of a Porphyrin Photosensitization Workshop,* Sep. 28-29, 1981, pp. 91-108.

Bertoloni et al., "Photosensitizing Activity of Water- and Lipid-Soluble Phthalocyanines on *Escherichia coli," FEMS Microbiology Letters* 71, 1990, pp. 149-156.

Gulliya et al., "Tumor Cell Specific Dark Cytotoxicity of Light-Exposed Merocyanine 540: Implications for Systematic Therapy Without Light," *Photochemistry and Photobiology,* 1990, vol. 52, No. 4, pp. 831-838.

Kennedy et al., "Photodynamic Therapy with Endogenous Protoporphyrin," *Journal of Photochemistry and Photobiology, B: Biology,* 1990, No. 6, pp. 143-148.

(56) References Cited

OTHER PUBLICATIONS

Gilliya et al., "Preactivation—A Novel Antitumor and Antiviral Approach," *European Journal of Cancer,* 1990, vol. 26, No. 5, pp. 551-553.
Chang et al., "Synegy between Preactivated Photofrin II and Tamoxifin in Killing Retrofibroma, Pseudomyxoma and Breast Cancer Cells," *European Journal of Cancer,* 1991, vol. 27, No. 8, pp. 1034-1038.
Doiron, D., "Instrumentation for Photodynamic Therapy," *Laser Systems for Photobiology and Photomedicine,* 1991, pp. 229-230.
Chanh et al., "Preactivated Merocyanin 540 Inactives HIV-1 and SIV: Potential Therapeutic and Blood Banking Application," *Journal of Acquired Immune Deficiency Syndrome,* 1992, pp. 188-195.
Gulliya et al., "Preactivation: A New Concept for Generation of Photoproducts for Potential Therapeutic Applications," *Seminars in Surgical Oncology,* Jul./Aug. 1992, vol. 8, No. 4, pp. 250-253.
Ma et al., "Effects of Light Exposure on the Uptake of Photofrin II in Tumors and Normal Tissues," *International Journal of Cancer,* 1992, vol. 52, pp. 120-123.
Pervaiz et al., "Protein Damage by Photoproducts of Merocyanine 540," *Free Radical Biology & Medicine,* 1992, vol. 12, pp. 389-396.
Labrousse et al., "Photodynamic Killing of *Dictyostelium disoideum,* Amoebae Mediated by 4', 5'-Diiodofluorescein Isothiocyanate Dextran. A Strategy for the Isolation of Thermoconditional Endocytosis Mutans," *Photochemistry and Photobiology,* 1993, vol. 67, No. 3, pp. 531-537.
Lytle et al., "Light Emitting Diode Source for Photodynamic Therapy," *SPIE,* 1993, vol. 1881, pp. 180-188.
Schlager et al., "Immunophototherapy for the Treatment of Cancer of the Larynx," *SPIE,* 1993, vol. 1881, pp. 148-158.
Nagae, T. et al., "Endovascular Photodynamic Therapy Using Mono-L-Aspartyl-Chlorin e6 to Inhibit Intimal Hyperplasi in Balloon-Injured Rabbit Arteries," *Lasers in Surgery and Medicine* 28: 381-388, 2001, Wiley-Liss, Inc.
Japan Patent Office, Official Office Action, counterpart JP Patent Application No. 2009-532583, mailed Jun. 26, 2013, 10 pages.

* cited by examiner

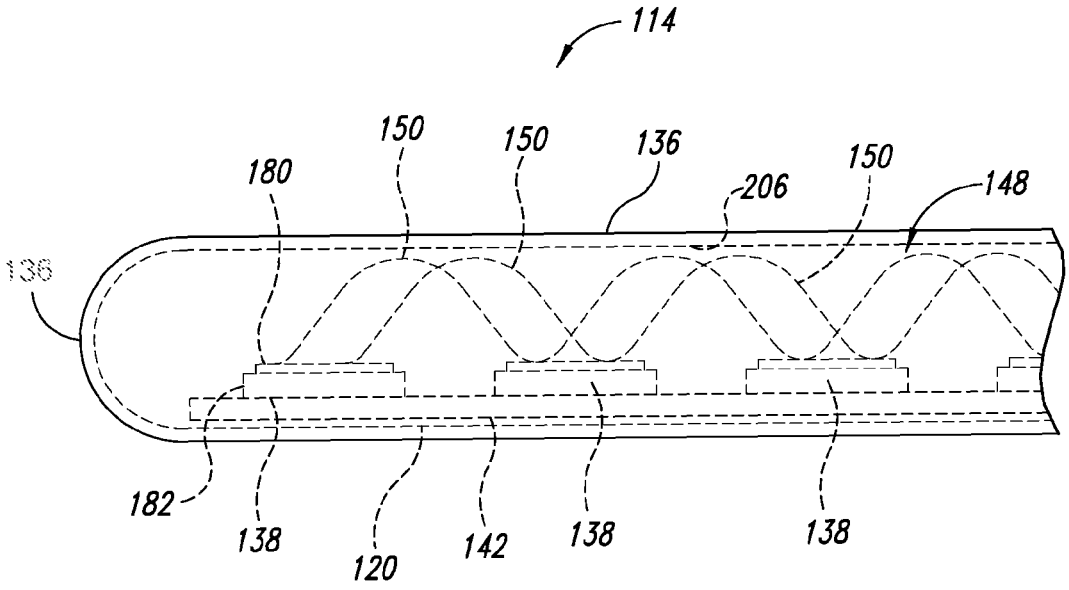
FIG. 2A
AMENDED

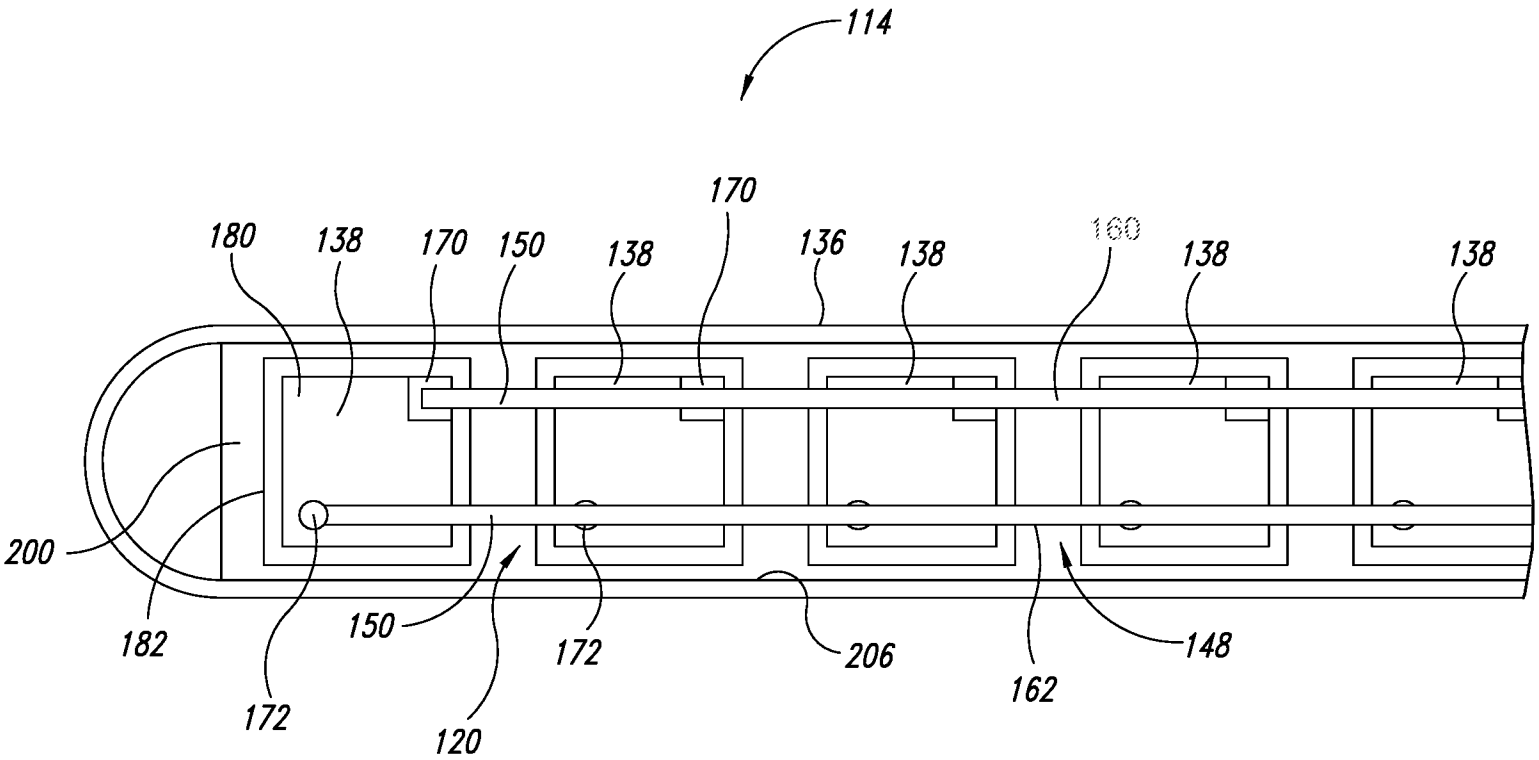
FIG. 2B
AMENDED

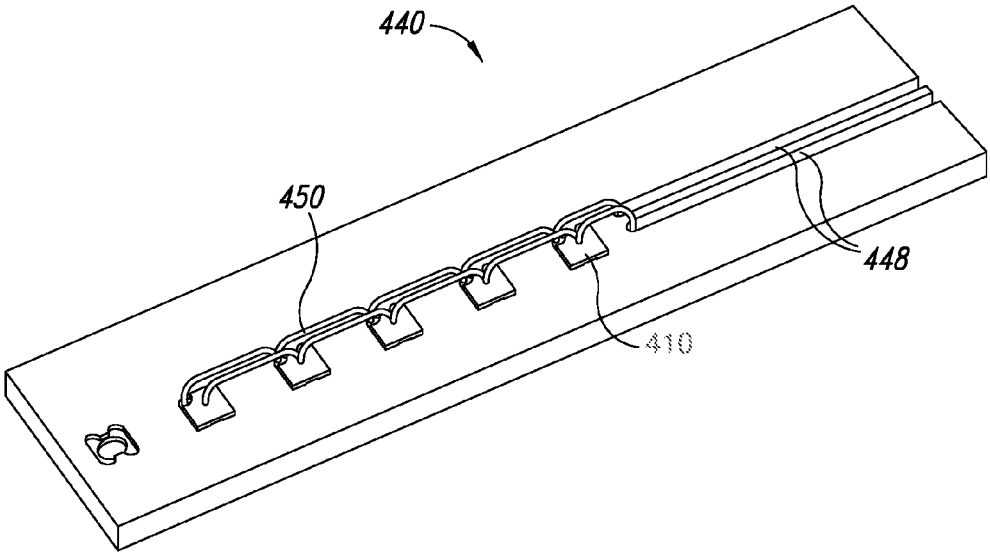
FIG. 20
AMENDED

LIGHT DELIVERY SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application claims the benefit under 35 U.S.C. §119 (e) of U.S. Provisional Patent Application No. 60/851,141 filed Oct. 11, 2006. This provisional application is incorporated herein by reference in its entirety.

BACKGROUND OF THE INVENTION

1. Field of the Invention

The present invention relates generally to a light delivery system useable for medical treatment, such as light therapy for the treatment of proliferative diseases.

2. Description of the Related Art

Light therapy includes photodynamic therapy (PDT) which is a process whereby light of a specific wavelength or waveband is directed toward a target cell or cells that have been rendered photosensitive through the administration of a photo-reactive, photo-initiating, or photosensitizing agent. This photo-reactive agent has a characteristic light absorption waveband and is commonly administered to a patient via intravenous injection, oral administration, or by local delivery to the treatment site. It is known that abnormal cells in the body may selectively absorb certain photo-reactive agents to a greater extent than normal for healthy cells. Once the abnormal cells have absorbed and/or molecularly joined with the photo-reactive agent, the abnormal cells can then be treated by exposing those cells to light of an appropriate wavelength or waveband that substantially corresponds to the absorption wavelength or waveband of the photo-reactive agent.

The objective of PDT may be either diagnostic or therapeutic. In diagnostic applications, the wavelength of light is selected to cause the photo-reactive agent to fluoresce as a means to acquire information about the targeted cells without damaging the targeted cells. In therapeutic applications, the wavelength of light delivered to the targeted cells treated with the photo-reactive agent causes the agent to undergo a photochemical reaction with oxygen in the localized targeted cells, to yield free radical species (such as singlet oxygen), which cause localized cell lysis or necrosis.

PDT has therefore proven to be an effective oncology treatment for destroying targeted cancerous cells. In addition, PDT has been proposed as a treatment for other ailments, some of which are described in Applicant's co-pending patent application U.S. Publication No. 2005/0228260 (U.S. patent application Ser. No. 10/799,357, which is hereinafter referred to as the '357 patent application).

One type of light delivery system used for PDT treatments comprises the delivery of light from a light source, such as a laser, to the targeted cells using a single optical fiber delivery system with special light-diffusing tips. This type of light delivery system may further include single optical fiber cylindrical diffusers, spherical diffusers, micro-lensing systems, an over-the-wire cylindrical diffusing multi-optical fiber catheter, and a light-diffusing optical fiber guidewire. This light delivery system generally employs a remotely disposed high-powered laser or solid state laser diode array, coupled to optical fibers for delivery of the light to the targeted cells. However, the use of laser light sources has several drawbacks, such as relatively high capital costs, relatively large size equipment, complex operating procedures, and safety issues in working with and around high-powered lasers.

The '357 patent application addresses some of these concerns and also addresses the desire to develop a light-generating apparatus that can be secured within a blood vessel or other orifice. The securing mechanism of such an apparatus would also be capable of removing light absorbent or light blocking materials, such as blood, tissue, or another object from the light path between the targeted cells and the light transmitters. Securing the apparatus within a blood vessel, for example, can be achieved with an inflatable balloon catheter that matches the diameter of the blood vessel when the balloon is inflated.

An introducing sheath having a lumen extending therethrough to create a passageway for insertion of other instruments into a patient's body through the sheath may be used with the light delivery system. One type of introducing sheath is described in another one of Applicant's co-pending patent applications, PCT Application No. PCT/US2005/032851. In general, this type of introducing sheath surrounds a penetrating device, which is introduced into the body and then removed, leaving the sheath behind as a passageway. One such instrument that can be inserted through the sheath is a light catheter for PDT treatment.

The light source for the light system used for PDT treatments may also be light emitting diodes (LEDs). Arranged LEDs form a light bar for the light system, where the LEDs may be either wire bonded or electrically coupled utilizing a "flip chip" technique that is used in arranging other types of semiconductor chips on a conductive substrate. Various arrangements and configurations of LEDs are described in U.S. Pat. Nos. 6,958,498; 6,784,460; and 6,445,011; and also in the '357 patent application.

BRIEF SUMMARY OF THE INVENTION

The embodiments described herein are generally related to a light delivery system usable for treating a patient by light therapy. As used herein, the term "light therapy" is to be construed broadly to include, without limitation, methods of treating a patient with light applied externally and/or internally. Light therapy can be used to treat various types of medical conditions, such as proliferative diseases including cancer. The light delivery system can have a relatively simple construction to reduce production time and fabrication costs. In some embodiments, the light delivery system comprises a catheter having a light bar, which is formed by a series of light sources positioned along a mounting base. The light bar is capable of delivering a sufficient amount of light to effectively treat target tissue. In one embodiment, the light bar is positioned within a distal tip of the catheter.

The distal tip is preferably flexible such that the distal tip can be twisted, bent, rolled or otherwise distorted. Thus, the distal tip can assume various positions during treatment without adversely affecting performance of the catheter or traumatizing the patient. In other embodiments, the distal tip is semi-rigid or rigid and is particularly well suited for delivery along somewhat linear delivery paths. The semi rigid or rigid distal tip can maintain its shape throughout the entire delivery process.

In some embodiments, a light delivery system for treating a patient includes a catheter having one or more light sources capable of transmitting light. The light sources can be energized in situ so as to output radiative energy. In some embodiments, the light sources are LEDs that form a light bar. The LEDs can be linearly spaced along a distal end of the catheter. In some variations, the LEDs are mounted to a mounting member which is sufficiently flexible to bend through an angle of at least 180°, 160°, 140°, 100°, 90°, 80°, or ranges encompassing such angles. In some variations, the mounting member is substantially optically transparent for transmitting light emitted by the LEDs.

In some embodiments, the light delivery system is a low profile catheter that is used to treat remote target region(s) of a patient. The catheter is sufficiently flexible so as to permit delivery along a tortuous path through the patient in order to locate a distal end of the catheter at the desired remote target region.

In some embodiments, a device for performing a medical treatment comprises a plurality of light sources capable of emitting light for treating a patient and a distal tip. The distal tip has an elongate base and is dimensioned for placement within a patient. The base can comprise a transmissive material. In some embodiments, the device can be flexible, semi rigid, and/or rigid.

In other embodiments, a device for performing a medical treatment is provided. The device comprises a plurality of light sources capable of emitting light for treating a patient; and a distal tip has an elongate base and is sufficiently flexible for placement within a patient, the base comprises a transmissive material such that a substantial portion of the light emitted from the plurality of light sources directed towards the base is transmitted through the base when the light sources are energized, the plurality of light sources being mounted upon the base.

In some embodiments, a method of producing a catheter for treating a patient is provided. The method comprises coupling a plurality of light sources onto a transparent elongate support, the light sources being spaced from one another; connecting the plurality of light sources such that a power source energizes the plurality of light sources; and placing an outer body around the elongate support and plurality of light sources mounted thereto, the outer body configured for positioning with a patient at a selected treatment location.

In some embodiments, a method of forming a light delivery system for treating a patient is provided. The method comprises placing an array of light energy sources in an array of holders of a fixture device, the light energy sources configured to treat a patient when energized in situ; electrically coupling the light energy sources together while the light energy sources are retained in the holders; after coupling the light energy sources together, removing the light energy sources from the fixture device; and encapsulating the array of light energy sources within an outer body, the outer body dimensioned for placement within a patient.

The light delivery systems described herein are well suited for other uses. For example, the light delivery systems can be used to improve lighting conditions during manufacturing processes, installation processes, repair processes, and the like. In some embodiments, the light delivery system can be used in combination with a viewing system (e.g., a camera, optical fibers, etc.). During operation of the viewing system, the light delivery system can provide adequate illumination for proper viewing. As such, the light delivery system can be used in the aerospace industry, electronics industry, construction, and other industries or settings that may require viewing in relatively small and/or remote locations having limited access, for example.

The light delivery systems can be snaked through conduits, piping, electrical components, walls, lumens, body vessels (e.g., the vascular system), and the like to provide flexibility in gaining access to regions of interest. For the sake of convenience, the light delivery systems will be discussed primarily with respect to medical uses.

In some embodiments, a light delivery apparatus can be used to treat a target site of tissue to promote tissue growth (e.g., cell division, cell growth or enlargement, etc.), increase the rate of healing, improve circulation, reduce or minimize pain, relieve stiffness, and the like. The light delivery apparatus can illuminate different types of tissue, such as muscle, bone, cartilage, or other suitable tissue, without using a treatment agent. One or more light sources of the light delivery apparatus can be configured to emit light with near-infrared or infrared wavelengths. This light itself can cause tissue growth. Alternatively, the light delivery apparatus can be used in combination with growth enhancers, growth factors, and the like.

The light delivery apparatus can also be used to destroy tissue by emitting energy that causes cell destruction. One or more energy sources of the light delivery apparatus can be activated to generate enough heat for cell destruction. If the energy sources are LEDs, the LEDs, when activated, can generate a sufficient amount of heat to cause tissue damage. In other embodiments, the energy sources can emit ultraviolet light that destroys the target cells. Such embodiments are especially well suited for destroying a thin layer of tissue without using a treatment agent or damaging an underlying layer of tissue.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles may not be drawn to scale, and some of these elements may be arbitrarily enlarged and positioned to improve drawing legibility.

FIG. 2A is a side elevational view of a distal end of the catheter assembly of FIG. 1, where the distal end includes an array of light sources mounted to an elongate base. Internal components are shown in dashed line.

FIG. 2B is a top schematic view of the distal end of the catheter assembly of FIG. 1.

FIG. 20 is a perspective view of the manufacturing tool of FIG. 19, where the manufacturing tool is holding an array of light sources connected by wires.

DETAILED DESCRIPTION OF THE INVENTION

Figure 1:
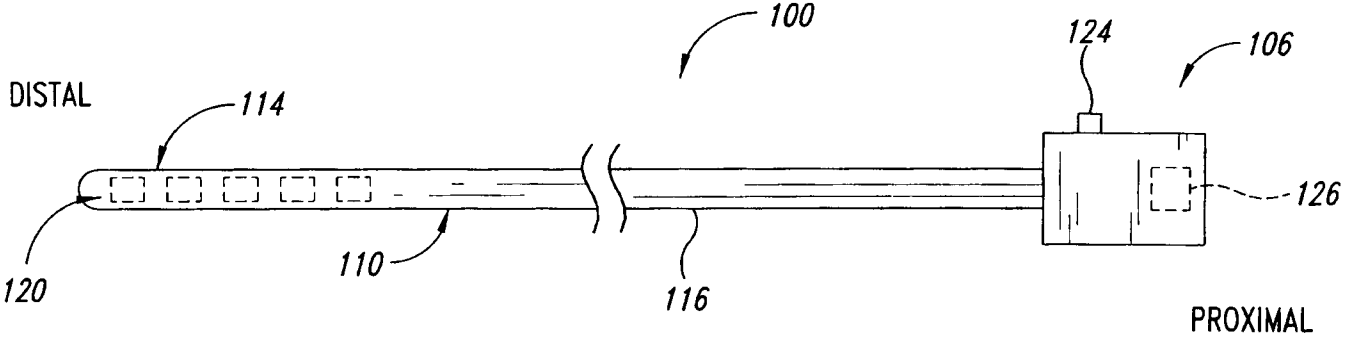
FIG. 1 is a side elevational view of a light delivery system having a catheter assembly and control system, according to one illustrated embodiment.

FIG. 1 is a side elevational view of a light delivery system 100 including a control system 106 and a catheter assembly 110 extending distally from and coupled to the control system 106, according to one embodiment. The light delivery system 100 can be used to perform various types of light therapy. Light therapy is broadly construed to include photo-activating or photo-exciting one or more target cells by subjecting the one or more target cells to one or more wavelengths of light that are approximately close to, if not equivalent to, at least one excitation wavelength of the target cells. This photo-excitation process can be used during an oncology treatment program, for example, to treat diseased or otherwise undesirable and/or cancerous target cells. It is understood that even if one cell is "targeted," it is possible that other cells in a vicinity of the targeted cell may also be subjected to light. The light delivery system 100 can be used to treat other types of abnormal cells.

The catheter assembly 110 includes a distal tip 114 and a catheter body 116 extending between the distal tip 114 and the control system 106. The distal tip 114 includes a transmission system 120 (shown in phantom) configured to output energy, such as radiant energy, suitable for treating a target region in the patient. Once the distal tip 114 is positioned at the target site, the control system 106 can be utilized for selectively controlling the output from the distal tip 114.

The control system 106 can include a controller 124 and a power supply 126 (shown in phantom in FIG. 1) in communication with the transmission system 120. The controller 124 can be operated to select the amount of radiant energy emitted by the light transmission system 120.

The illustrated internal power supply 126 is a battery, such as a lithium battery. In other embodiments, the light delivery system 100 is powered by an AC power source, such as an electrical outlet typically found at a hospital, medical facility, or other suitable location for performing light therapy. The control system 106 can include a power cord that can be connected to the AC power source. Accordingly, various types of internal and/or external power sources can be utilized to power the light delivery system 100.

The catheter assembly 110 of FIG. 1 has a low profile configuration suitable for percutaneous advancement and navigation within a patient. Such a construction allows convenient delivery and placement of the distal tip 114 at remote locations within a patient, unlike catheters with larger light bars. The catheter assembly 110 can also be dimensioned for other means of delivery and placement. For example, the catheter assembly 110 can be configured for external light delivery (e.g., transcutaneous or transdermal delivery). This external catheter assembly can be larger than the percutaneously delivered catheter assembly described above. Accordingly, the dimensions (e.g., the axial length, cross-sectional width, etc.) the catheter assembly 110 can be selected based upon the accessibility of the target tissue.

The catheter assembly 110 can have a cross-sectional width that is less than about 1.25 mm. In some embodiments, the catheter assembly 110 has a cross-sectional width that is less than about 1 mm. In some embodiments, the catheter assembly 110 has a cross-sectional width that is less than about 0.80 mm. In some embodiments, the catheter assembly 110 has a cross-sectional width that is less than about 0.75 mm. In some embodiments, the catheter assembly 110 has a cross-sectional width that is less than about 0.70 mm. The distal tip can have a cross-sectional width less than about 10 mm, 5 mm, 1.5 mm, 1.25 mm, 1.0 mm, 0.75 mm, 0.5 mm, and ranges encompassing such widths. Other dimensions are also possible.

In some embodiments, the light delivery system 100 can be used as an adjunct during another medical procedure, such as minimally invasive procedures, open procedures, semi-open procedures, or other surgical procedures that preferably provide access to a desired target region. Many times, the access techniques and procedures used to provide access to a target region can be performed by a surgeon and/or a robotic device, such as robotic systems used for performing minimally invasive surgeries. Those skilled in the art recognize that there are many different ways that a target region can be accessed. Optionally, the light delivery system 100 is used with guidewires, delivery sheaths, delivery devices (e.g., endoscopes, bronchoscopes, optical instruments, etc.), introducers, trocars, biopsy needle, or other suitable medical equipment. If the target treatment site is at a distant location in the patient, delivery devices should be used for convenient navigation through tortuous body lumens or other anatomical structures in the patient. The flexible light delivery system 100 can be easily positioned within the patient using, for example, steerable devices, such as endoscopes, bronchoscopes, and the like. Semi-rigid or rigid light delivery systems 100 can be delivered using trocars, access ports, rigid delivery sheaths using semi-open procedures, open procedures, or other delivery tools/procedures that provide a somewhat straight delivery path, for example. Advantageously, the semi-rigid or rigid system 100 can be sufficiently rigid to displace internal tissue to help facilitate light delivery to the target tissue. When inserted in the patient, the system 100 can be easily rotated and advanced axially while maintaining its configuration.

FIGS. 2A and 2B show the distal tip 114 including the transmission system 120 encapsulated in a protective outer body 136. When the transmission system 120 is activated, radiant energy is delivered from the transmission system 120 through the outer body 136 to the desired target region, preferably tissue near the outer body 136 such that an effective amount of radiant energy reaches the target region.

The transmission system 120 includes one or more energy sources 138 mounted onto a base 142. As used herein, the term "energy source" is a broad term and includes, but is not limited to, energy sources capable of emitting radiant energy, such as electromagnetic energy. Non-limiting exemplary energy sources can be light sources capable of emitting visible light waves, non-visible light waves, and combinations thereof. The energy sources can be LEDs (such as edge emitting LEDs, surface emitting LEDs, super luminescent LEDs), laser diodes, or other suitable energy sources.

FIGS. 2A and 2B illustrate a linear array of LEDs 138 spaced apart along the length of the distal tip 114. In the illustrated embodiment, the LEDs 138 are coupled upon a longitudinally extending upper face 200 of the elongate base 142. A conductive connector 148 interconnects the LEDs 138 so as to distribute electrical energy between the LEDs. The term "conductive connector" is a broad term and includes, without limitation, lead(s), wire(s) (preferably flexible wires), bus bar(s), a conductive film or ink applied to a substrate, or other conductor suitable for electronically coupling the LEDs 138 to the control system 106. In the illustrated embodiment of FIGS. 2A and 2B, the conductive connector 148 is a plurality of leads 150 formed by a pair of wires 160, 162 extending above and coupled to the LEDs 138, thereby forming a complete circuit.

The LEDs 138 can be arranged in parallel, series, or combinations thereof. For example, some LEDs 138 can be arranged in series while other LEDs are arranged in parallel. As such, various circuit configurations can be used when mounting the LEDs 138 to the base 142. Exemplary non-limiting embodiments of circuits are discussed below in detail.

With continued reference to FIG. 2B, each LED 138 has electrodes 170, 172 coupled to the wires 160, 162, respectively. Each LED 138 can also include one or more layers *180* (e.g., GaN layers, AlGaN layers, InGaN layers, [AlInGap] *AlInGaP* layers and/or AlInGaN layers) disposed between the electrodes 170, 172 and a substrate 182, as shown in FIG. 2A. In the illustrated embodiment, the substrate 182 is a transmissive substrate. For example, the substrate 182 can be optically transparent to the light emitted from the layer(s) described above.

The illustrated LEDs 138 can emit appropriate wavelength(s) or waveband(s) suitable for treating the patient, with or without using a treatment agent. If a treatment agent (e.g., a photo-reactive or photosensitive agent) is utilized, the LEDs 138 preferably emit radiation wavelength(s) or waveband(s) that corresponds with, or at least overlap with, the wavelength(s) or waveband(s) that excite or otherwise activate the agent. Photosensitive agents can often have one or more absorption wavelengths or wavebands that excite them to produce substances which damage, destroy, or otherwise treat target tissue of the patient. For example, the LEDs 138 can be configured to emit light having a wavelength or waveband in the range from about 400 nanometers to 1,000 nanometers. In some embodiments, the LEDs 138 emit a wavelength or waveband in the range from about 600 nanometers to about 800 nanometers. In some embodiments, the LEDs 138 emit a wavelength or waveband in the range from about 600 nanometers to about 700 nanometers. In one embodiment, for example, the LEDs 138 emit radiation with a peak wavelength of 664 nanometers plus or minus 5 nanometers.

Each LED 138 of the distal tip 114 can be configured be to emit the same wavelength or waveband. However, LEDs having different wavelengths or wavebands can be used to provide varying outputs. These LEDs 138 can be activated simultaneously or at different times depending on the desired treatment. The various LEDs 138 can also be activated and deactivated in a pulsed sequence. For example, the LEDs 138 may form two halves of the light array which are alternately turned on and off. Alternately, the system may be programmed to selectively activate and deactivate different selected segments of LEDs 138 along the length of the light bar. In this manner, a treatment protocol, for example causing the LEDs to be lit in a certain sequence, at a particular power level for a selected period of time, may be programmed into the control system 106.

The distal tip 114 can have any number of LEDs 138. In the illustrated embodiment, five LEDs are positioned generally along the longitudinal axis of the distal tip 114. However, a higher or lower number of LEDs can be selected based on the desired energy output, emitted wavelength(s) and/or waveband(s), surface area of target site, desired level of energy penetration, and other treatment parameters. In some embodiments, for example, about 60 LEDs are spaced along the distal tip 114 at a 1 mm pitch. In other embodiments, the LEDs can be at a pitch in the range of about 1.5 mm to about 0.5 mm. In some embodiments, less than 70 LEDs are spaced along the distal tip 114. In other embodiments, less than 50 LEDs are spaced along the distal tip 114. In yet other embodiments, less than 40 LEDs are spaced along the distal tip 114. The illustrated LEDs 138 are evenly spaced and form a single row; however, other LEDs arrangements are possible. For example, the distal tip 114 can include a matrix of LEDs 138.

As described above in connection with FIGS. 2A and 2B, the LEDs 138 are mounted upon the upper face 200 of the base 142. Any suitable mounting means can be employed to temporarily or permanently couple the LEDs 138 onto the base 142. For example, adhesives, bonding material, fasteners, solder, or other coupling means can securely couple the LEDs 138 to the base 142. The mounting means can be optically transparent in order to transmit light generated by the LEDs 138 to the base 142 which, in turn, transmits light that ultimately reaches the patient. In the illustrated embodiment of FIGS. 2A and 2B, optically transparent epoxy permanently couples the linearly spaced LEDs 138 to the upper face 200.

With continued reference to FIGS. 2A and 2B, the base 142 is an elongate member that extends longitudinally along the distal tip 114, and provides a relatively large mounting area on the upper face 200 for convenient placement of the LEDs 138. The base can be a support substrate sized to hold any number of LEDs.

The base 142 is preferably sufficiently flexible so as to permit enough distortion of the distal tip 114 for delivery along a tortuous path. The base 142 can be twisted, bent, rolled, and/or otherwise distorted, preferably without any appreciable damage to the base 142 and/or LEDs 138 mounted thereto. In some embodiments, the base 142 can be moved through an angle of 220°, 180°, 150°, 130°, 90°, 70°, 50°, and ranges encompassing such angles.

In some embodiments, the base 142 is a thin, flat strip of a flexible material. The thin base 142 helps reduce the profile of the light transmission system 120 and, consequently, the overall cross-sectional width of the distal tip 114. Furthermore, the base 142 can be easily bent and twisted to allow navigation along tortuous paths within the patient, thus permitting flexibility in selecting treatment protocols.

Figure 3A:
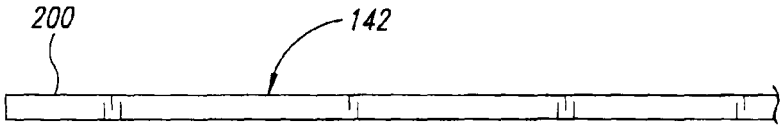
FIG. 3A is a side elevational view of the elongate base of FIG. 2A.
Figure 3B:
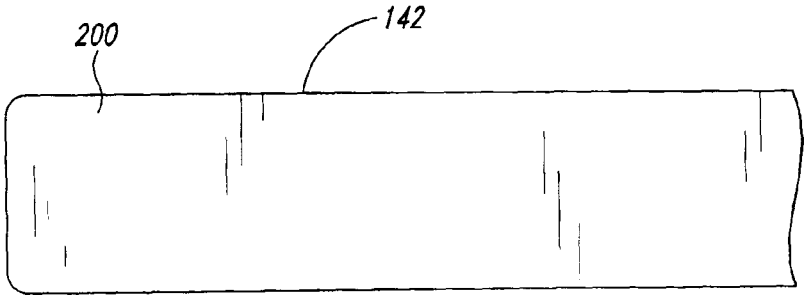
FIG. 3B is a top elevational view of the elongate base of FIG. 3A.
Figure 3C:
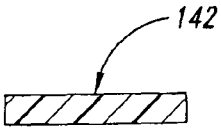
FIGS. 3C to 3E are axial cross-sectional views of different embodiments of bases suitable for carrying an array of light sources.
Figure 3D:
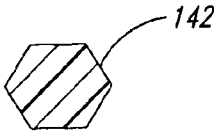
Figure 3E:
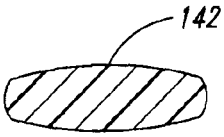

The base 142 can have a polygonal axial cross-section (e.g., a rectangular cross-section), elliptical cross-section, or other suitable axial cross-section. FIGS. 3C to 3E illustrate various axial cross-sections of the base 142.

Various materials can be used to construct the base 142. Flexible, semi-rigid, and/or rigid bases 142 can be made of rubber, composite materials, thermoplastics, polymers (e.g., polyester, polyethylene terephthalate (PET), polypropylene, polyethylene naphthalate (PEN), and combinations thereof. In one embodiment, the base 142 comprises a somewhat transparent material, preferably an optically transparent polyester. At least one wavelength of light emitted by the LEDs can pass through the base 142, as discussed in more detail below.

The material(s) forming the base 142 can be selected to achieve the desired structural properties, thermal properties, electrical properties, optical properties, and durability. For example, to dissipate heat generated by the LEDs 138, the base 142 can comprise a heat conductive material that can act as a heat sink for conducting heat away from the LEDs in order to maintain the light transmission system 120 at an appropriate operating temperature. Additionally, one or more ribs, stiffeners, joints, reinforcement members, strain relief elements, or other structural elements can be added to the base 142 to achieve the desired properties. As noted above, the base 142 may be somewhat rigid for some medical applications. For example, a base 142 in distal tip 114 for applying light externally to the patient may be a rigid member comprised of metal, rigid plastic, or other suitably stiff material.

As mentioned above, the base 142 can comprise a transmissive material to allow light emitted from the LEDs to pass therethrough. Thus, the base 142 advantageously supports the LEDs 138 while also permitting the passage of light therethrough to increase the efficacy of the light treatment and decrease power consumption. Further, the base 142 can be relatively large for an enlarged LED mounting zone without appreciably reducing the amount of light reaching the target tissue. This results in easy placement of the LEDs.

Suitable transmissive materials include, but are not limited to, polymers such as polyester, PET, polypropylene, combinations thereof and the like. One or more layers of material can form the base 142. Preferably, a substantial amount of the light directed from the LEDs 138 towards the base 142 is transmitted through the base 142. In some embodiments, at least 40% of the light emitted towards the base 142 is transmitted therethrough. In some embodiments, at least 50% of the light directed towards the base 142 is transmitted therethrough. In some embodiments, at least 60% of the light directed towards the base 142 is transmitted therethrough. In some embodiments, at least 70% of the light directed towards the base 142 is transmitted therethrough. In some embodiments, at least 80% of the light directed towards the base 142 is transmitted therethrough. In some embodiments, at least 90% of the light directed towards the base 142 is transmitted therethrough. Additionally, one or more light passageways, through-holes, windows, or other structures can be formed in the base 142 to increase the amount of light passing through the base 142.

The base 142 can optionally include one or more opaque materials that can inhibit or prevent one or more wavelengths or wavebands from passing therethrough. Opacification agents, additives, coatings, or combinations thereof can be utilized to render the base 142 (or portion thereof) somewhat opaque. In some embodiments, the opacification agents include, but are not limited to, dyes, pigments, metal particulates or powder, or other materials that can be coated onto, disbursed throughout, or otherwise disposed in the base 142. If desired, the base 142 can function as a filter so as to inhibit or prevent one or more wavelengths or wavebands from reaching the patient's tissue.

In some embodiments, the base 142 extends proximally from the distal tip 114 along the entire length of the catheter body 116. In other embodiments, a proximal end of the base 142 is positioned distally of the proximal end of the catheter assembly 110. For example, the proximal end of the base 142 can be positioned at some point along the catheter body 116, or within the distal tip 114.

As shown in FIGS. 2A and 2B, the light transmission system 120 is housed within the outer body 136, as discussed above. The outer body 136 is preferably transmissive so as to transmit radiation emitted from the light transmission system 120. For example, the outer body 136 can be made of the same material(s) forming the base 142. During advancement through the patient's body and placement at the target site, external forces may be applied to the distal tip 114. Accordingly, the outer body 136 can be made of a material suitable for limiting or preventing undesirable damage to the light transmission system 120.

The outer body 136 can define a chamber 206 sized to accommodate the light transmission system 120. In some embodiments, an encapsulate (e.g., a polymer) can be used to fill the chamber 206 in order to minimize or prevent movement of the light transmission system 120 relative to the outer body 136. Alternatively, the outer body 136 can define a hollow chamber 206 which can increase the overall flexibility of the distal tip 114. Optionally, the outer body 136 can be an expandable member, such as those disclosed in the '357 patent application, which is hereby incorporated by reference in its entirety. The chamber 206 can be filled with an inflation fluid to inflate the outer body 136. In other embodiments, the outer body 136 is a monolithic protective outer member, such as a member molded over the light transmission system. Accordingly, the outer body 136 can have a one-piece or multi-piece construction.

Figure 4:
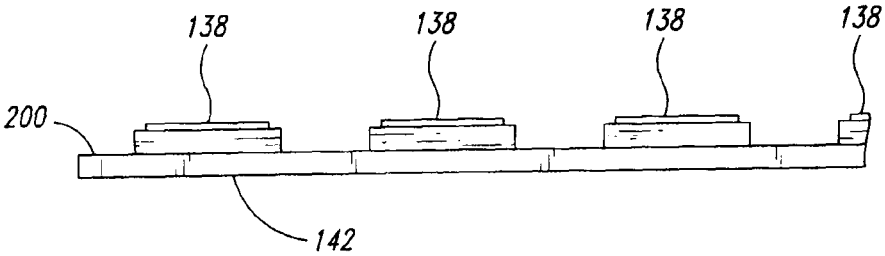
FIG. 4 is a side elevational view of an array of light sources mounted to the base of FIGS. 3A and 3B.

FIGS. 3A, 3B, and 4-5B illustrate one embodiment of a process to produce a distal tip 114 using wire bonding techniques. FIGS. 3A to 3E show the base 142 which is the starting material for forming the distal tip 114. LEDs 138 are attached to the upper surface 200 of the base 142, as shown in FIG. 4. The base 142 maintains the desired spacing between the mounted LEDs 138 while the wire bonds 150 are formed. In this manner, the base 142 helps to improve the tolerances between the LEDs, even though the LEDs may be subjected to subsequent processing. In the illustrated embodiment of FIG. 5A, for example, the pair of wires 160, 162 are connected to the electrodes 170, 172, respectively, with solder while the LEDs 138 remain securely mounted to the base 142. Accordingly, the base 142 can function as a LED holder thus reducing fabrication time and improving tolerances. Additionally, the base 142 can be made of a low cost material (e.g., polyester) that is ultimately integrated into the distal tip assembly 114 thereby reducing material waste and cost.

Figure 5A:
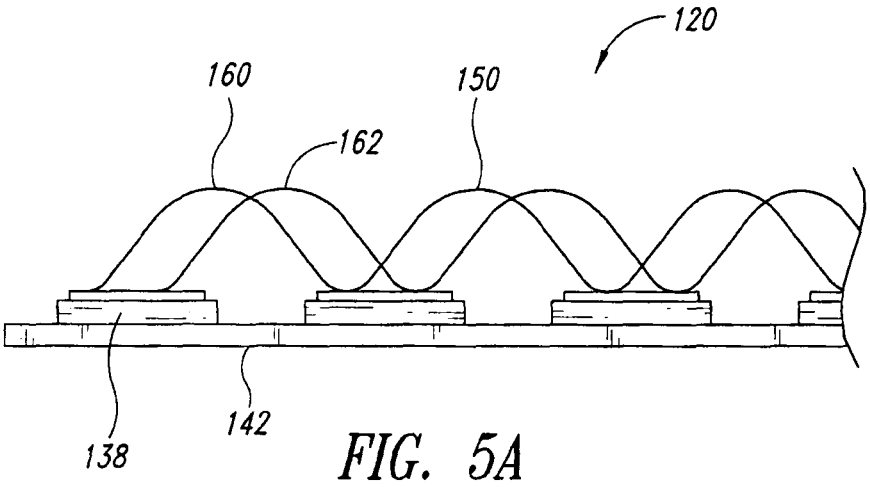
FIGS. 5A and 5B are side and top elevational views, respectively, of a light transmission system, where wires connect adjacent light sources.
Figure 5B:
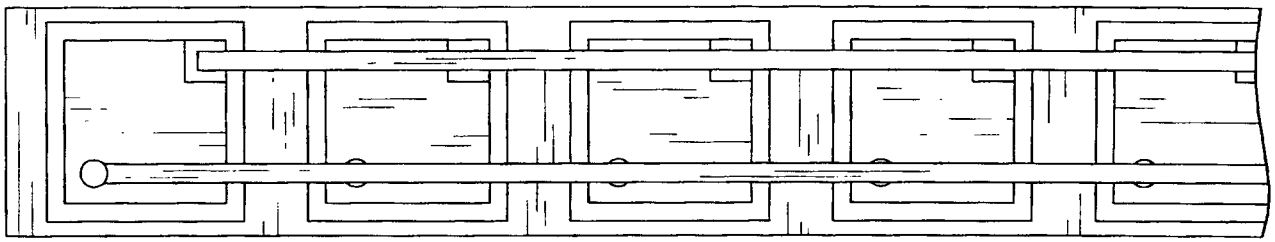

After assembling the transmission system 120 (as shown in FIGS. 5A and 5B), the outer body 136 can be formed by various molding techniques. For example, the outer body 136 can be formed through a molding process (e.g., an injection molding process, compression molding process, etc.), thermoforming, machining process, or combinations thereof. In some embodiments, the light transmission system 120 can be placed in a mold cavity corresponding to the desired shape of the outer body 136. To oversold the light transmission system 120, a molten polymer can be injected into the mold cavity. Alternatively, the outer body 136 can be a preformed hollow member. The light transmission system 120 can be inserted into the member until the distal tip 114 is fully assembled.

Figure 6:
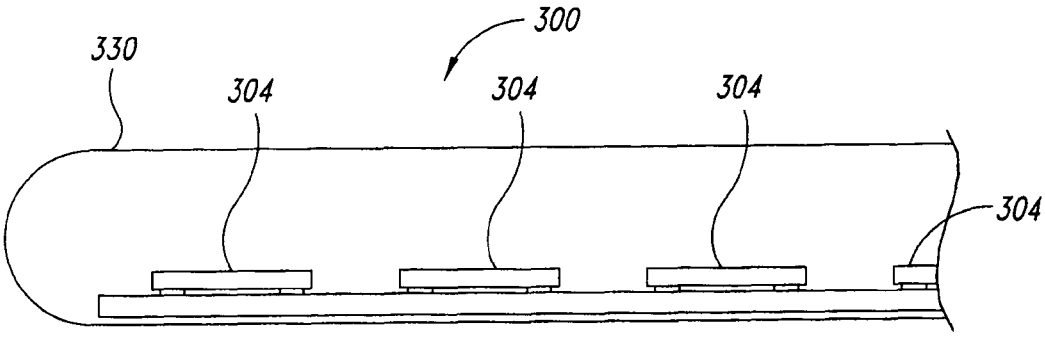
FIG. 6 is a side schematic view of a distal end of a catheter assembly having light sources which are flip chip mounted to an elongate base, according to one illustrated embodiment.

FIG. 6 shows another embodiment of a distal tip that can be incorporated into the light delivery system 100 of FIG. 1. The distal tip 300 of FIG. 6 may be generally similar to the distal tip 114 illustrated in FIG. 1, except as further detailed below.

The distal tip 300 of FIG. 6 has an array of LEDs 304 that are mounted in a flip chip arrangement. A flip chip is one type of integrated circuit (IC) chip mounting arrangement that does not require wire bonding between chips (e.g., the chip mounting arrangement described above in connection with FIGS. 1-5B). Thus, wires or leads that typically connect a chip/substrate having connective elements can be eliminated to further reduce the profile of the distal tip. That is, the distal tip 300 can have a lower profile than the distal tip 114 and is well suited for delivery along narrow passageways. By way of example, the distal tip 114 of FIG. 1 can have a diameter in the range of about 1.5 mm to about 1.2 mm, although other diameters are also possible. The flip chip mounted distal tip 300 of FIG. 6 has a diameter in the range of about 0.8 mm to about 0.7 mm. In some embodiments, the distal tip 300 has a diameter of about 0.74 mm. Thus, the distal tip 300 can be delivered along relatively narrow delivery paths, while providing the same output as the wire bonded distal tip 114.

FIGS. 7-10 illustrate one embodiment of a process to produce a distal tip 300 of FIG. 6 having flip chip mounted LEDs. Generally, instead of wire bonding described above, solder beads or other elements can be positioned or deposited on chip pads such that when the chip is mounted upside-down in/on the substrate, electrical connections are established between conductive traces of the substrate and the chip.

Figure 7:
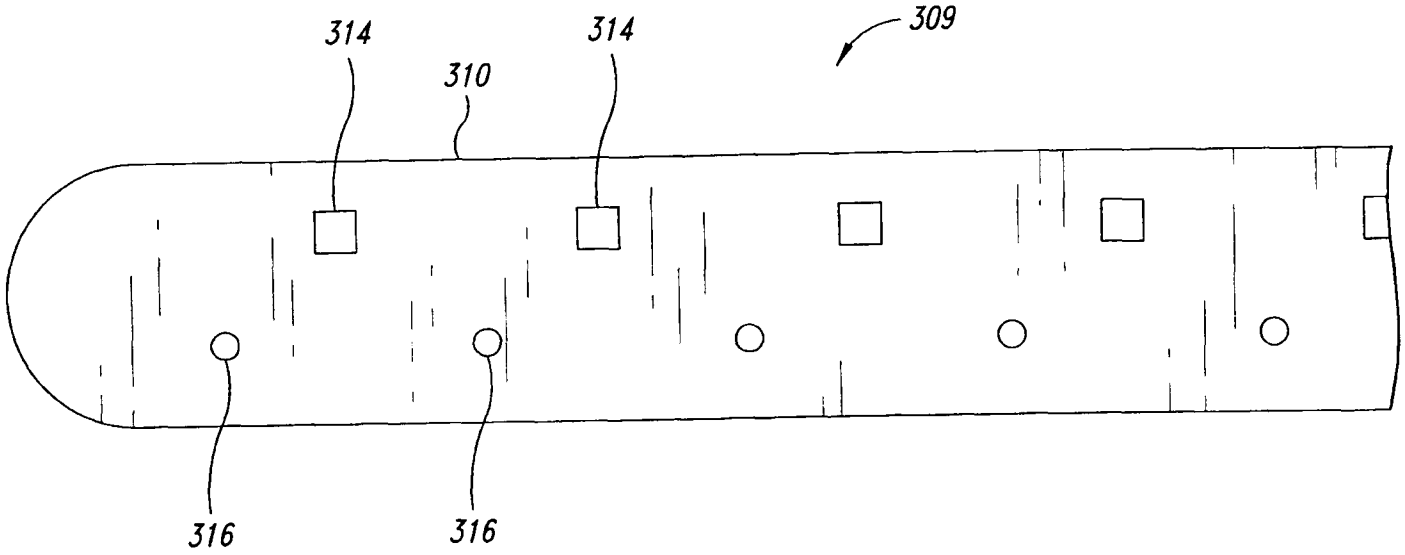
FIG. 7 is a top elevational view of the base of FIG. 6.
Figure 8A:
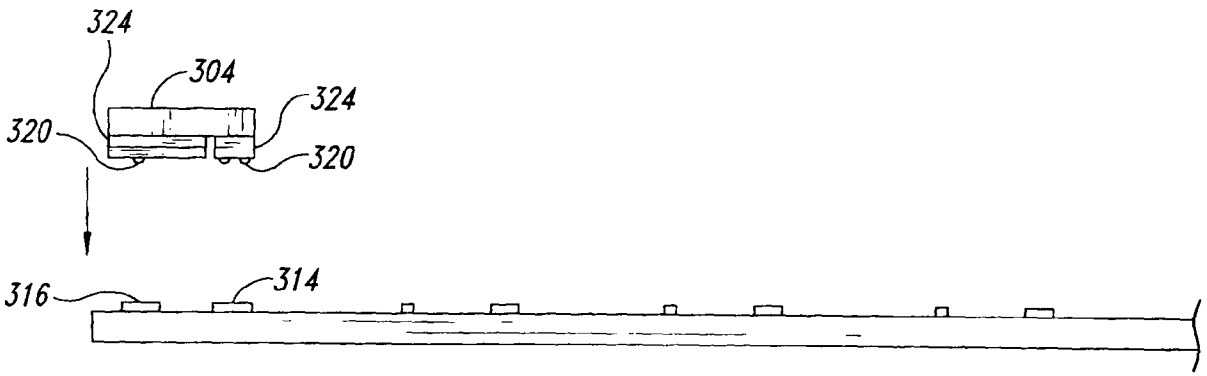
FIG. 8A is a side elevational view of one light source positioned above the base of FIG. 7.
Figure 8B:
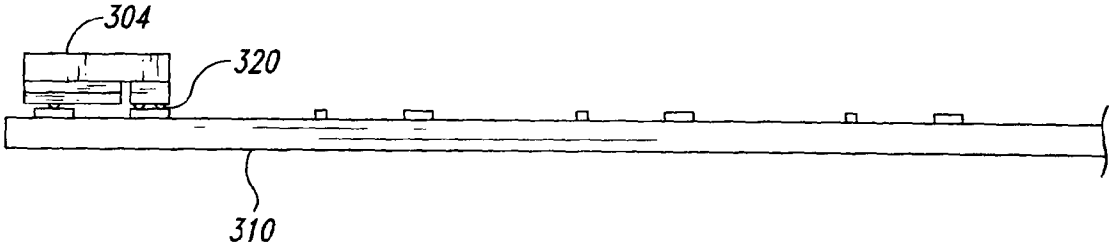
FIG. 8B is a side elevational view of the light source of FIG. 8A after the light source has been assembled with the base.
Figure 9:
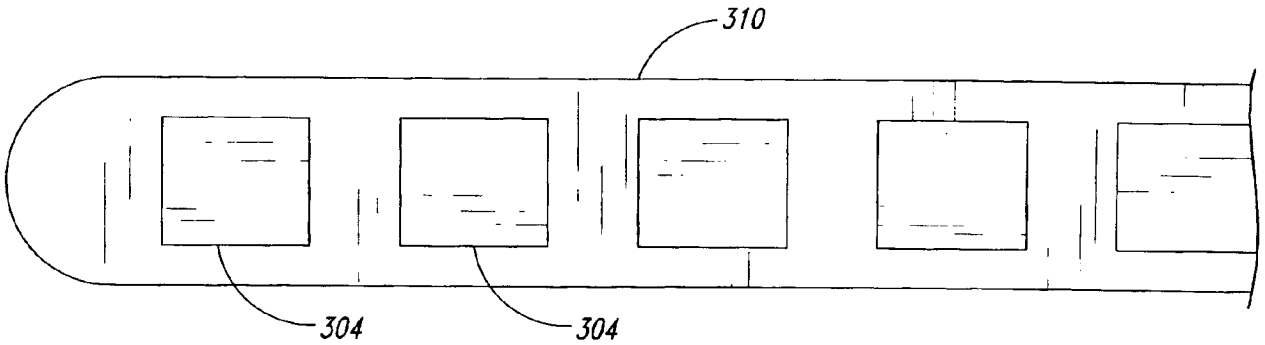
FIG. 9 is a top elevational view of an array of light sources linearly mounted to an upper face of the base.

FIG. 7 illustrates a circuit 309 including a base 310 and an array of conducting traces or electrodes 314, 316 suitable for flip chip mounting. As shown in FIG. 8A, an LED 304 can be positioned above the pair of the traces 314, 316. Solder beads 320 are formed on the electrodes 324 of the LED 304 such that when the LED 304 is lowered onto the circuit 309, preformed solder beads can electrically and mechanically connect the LED to the traces 314, 316 of the base 310. After one or more of the LEDs 304 are placed upon the base 310, the solder beads 320 can be heated or thermally treated until the solder securely couples the LEDs 304 to the base 310, as shown in FIG. 8B. After the LEDs 304 are mounted onto the base 310, an outer body 330 can be formed in the manner described above.

The base 310 of FIG. 7 can comprise the same materials as the base 142 of FIGS. 2A and 2B. However, the base 310 can also be formed of other materials. For example, the base 310 can be formed of a polyamide material (e.g., polyimide flex) that is especially well-suited for flip chip mounting arrangements. To increase the amount of light passing through the base 310, one or more light passageways can be formed in the base 310. A light passageway can be a through-hole, window, transmissive material(s), or other suitable element for increasing the amount of light traveling through the base 310. The number and/or size of the light passageways can be increased or decreased to increase or decrease, respectively, the amount of transmitted light.

Figure 10:
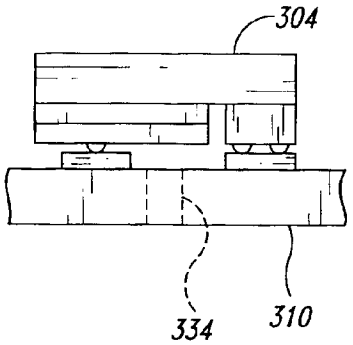
FIG. 10 is a side elevational view of a light source mounted above an aperture extending through a base, according to one illustrated embodiment.

FIG. 10 shows a light passageway 334 (shown in phantom) in the form of a through-hole in the base 310. As such, light emitted from the LED 304 can pass easily through the base 310 via the light passageway 334. The light passageway 334 can be formed before, during, or after the LED 304 is mounted to the base 310. For example, the LED 304 can be mounted onto a pre-formed perforated base 310. Preferably, the light passageways 334 are positioned so as to effectively transmit light from the LED through the base 310.

Figure 11:
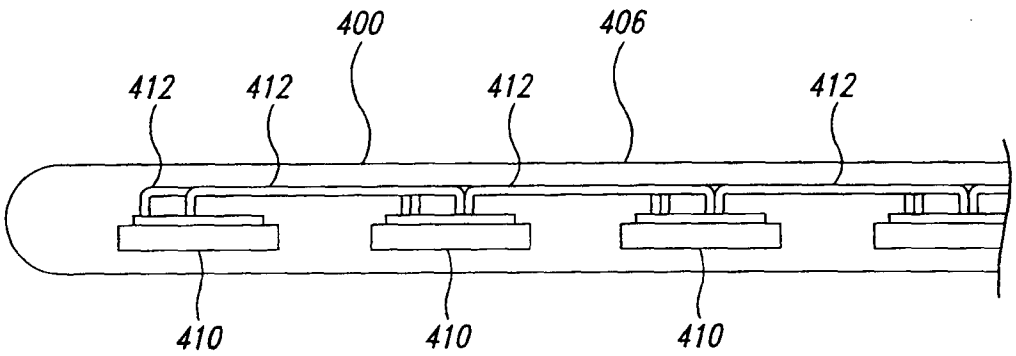
FIG. 11 is a side schematic view of a distal end of a catheter, where an array of light sources is within an encapsulant.

FIG. 11 shows another distal tip that can be incorporated into the light delivery system 100 of FIG. 1. The distal tip 400 may be generally similar to the distal tip 114 illustrated in FIG. 1, except as further detailed below.

The distal tip 400 of FIG. 11 has a light transmission system including a plurality of light sources 410 that are wire bonded together by a plurality of conductive elements 412 in the form of leads. Advantageously, the distal tip 400 can be formed without utilizing the support bases as described above. The light transmission system can be directly mounted in the outer body 406, so as to reduce the number of components forming the tip. Additionally, the support bases described above may inhibit the passage of light therethrough thereby limiting the illumination of the tissue. Thus, the distal tip 400 can be used to deliver an increased amount of light.

The stress on the leads 412 of FIG. 11 may be less than the stress experienced by the leads 150 of FIGS. 2A and 2B because the base 142 of FIG. 2A may help define the bend axis of distal tip 114. As such, the base 142 can cause the bend axis to be spaced an undesirable distance from the leads resulting in increased axial stresses in the leads when the distal tip 114 is bent. In FIG. 11, however, a support base does not move the bend axis away from the leads 412. Accordingly, the leads 412 can be positioned near or at the neutral axis of the distal tip 400, thereby reducing or eliminating axial stresses on the leads. In some embodiments, leads 412 can act as pivot points defining the bending axis of the distal tip 400, if desired.

Figure 12A:
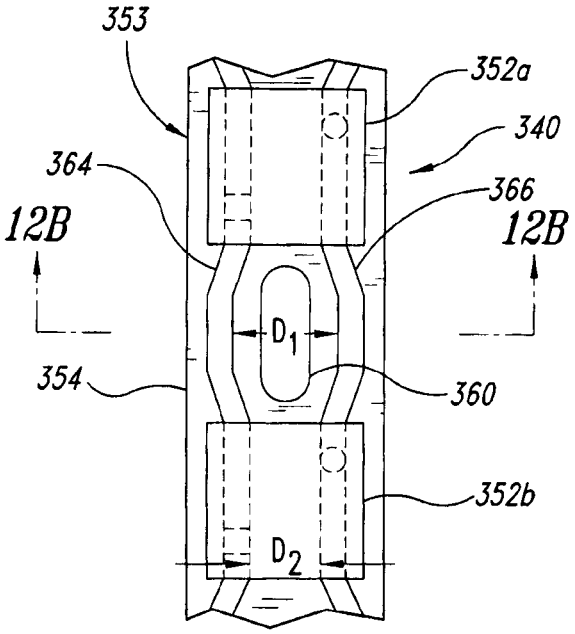
FIG. 12A is a top elevational view of a portion of a light transmission system, according to one illustrated embodiment.
Figure 12B:
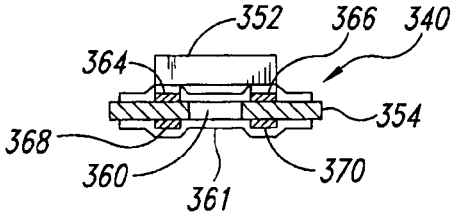
FIG. 12B is a cross-sectional view of the light transmission system of FIG. 12A taken along line 12B-12B.
Figure 13:
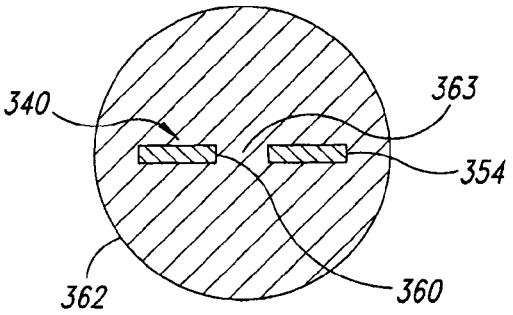
FIG. 13 is an axial cross-sectional view of the light transmission system of FIG. 12A, where the light transmission system is within an encapsulant.

FIGS. 12A and 12B illustrate a light transmission system 340 having a plurality of flip chip mounted light sources 352A, 352B coupled to a circuit 353. A base 354 of the circuit 353 defines one or more locking structures 360 for enhancing coupling between an encapsulant and the light transmission system 340. As shown in FIG. 13, an encapsulant 362 can surround the light transmission system 340, and a portion 363 of the encapsulant 362 can pass through the locking structure 360 extending through the base 354. As such, the locking structure 360 can minimize, limit, or prevent movement between the light transmission system 340 and encapsulant 362. Additionally, the locking structure 360 can advantageously inhibit or prevent delamination of the encapsulant 362 from the base 354.

The illustrated locking structure 360 of FIGS. 12A to 13 is a through-hole having an elongated axial cross-section. In some non-limiting exemplary embodiments, the locking structure 360 has a width of about 0.005 inch (0.127 mm) and a length of about 0.011 inch (0.28 mm) and is located between two light sources 352A, 352B, each having a length and width of about 0.014 inch (0.356 mm). The size of the locking structure 360 can be increased or decreased to increase or decrease, respectively, the amount of the encapsulant 363 extending through the base 354. In other embodiments, the locking structure 360 can have a polygonal (including rounded polygonal), elliptical, circular, or any other suitable cross-section. A drilling process, machining process, or other suitable process can be used to form the structure 360.

With reference again to FIG. 12A, the light transmission system 340 includes a pair of generally longitudinally-extending traces 364, 366 interposed between the light sources 352A, 352B and base 354. The traces 364, 366 interconnect adjacent pairs of light sources 352A, 352B. To accommodate an enlarged locking structure 360, the distance between portions of the traces 364, 366 can be increased, as shown in FIG. 12A. In the illustrated embodiment of FIG. 12A, the distance D1 between the traces 364, 366 is greater than the distance D2 between the portions of the traces 364, 366 adjacent or beneath the light sources 352A, 352B. The spacing between the traces 364, 366 can be selected based on the size, position, and/or configuration of the locking structure 360.

The other light transmission systems disclosed herein can also include one or more locking structures. For example, the base 142 of FIG. 2A can include one or more locking structures interposed between adjacent pairs of wire bonded LEDs. Thus, locking structures can be used with wire bonded LEDs, flip chip LEDs, and other chip mounting arrangements.

With continued reference to FIGS. 12A and 12B, the traces 364, 366 are delivery traces connecting the light sources 352A, 352B. The base 354 is interposed between the delivery traces 364, 366 and return traces 368, 370. A coverlay 361 (shown removed in FIG. 12A) can overlay at least a portion of both the base 354 and the traces 364, 366, 368, 370, as shown in FIG. 12B.

Figure 14A:
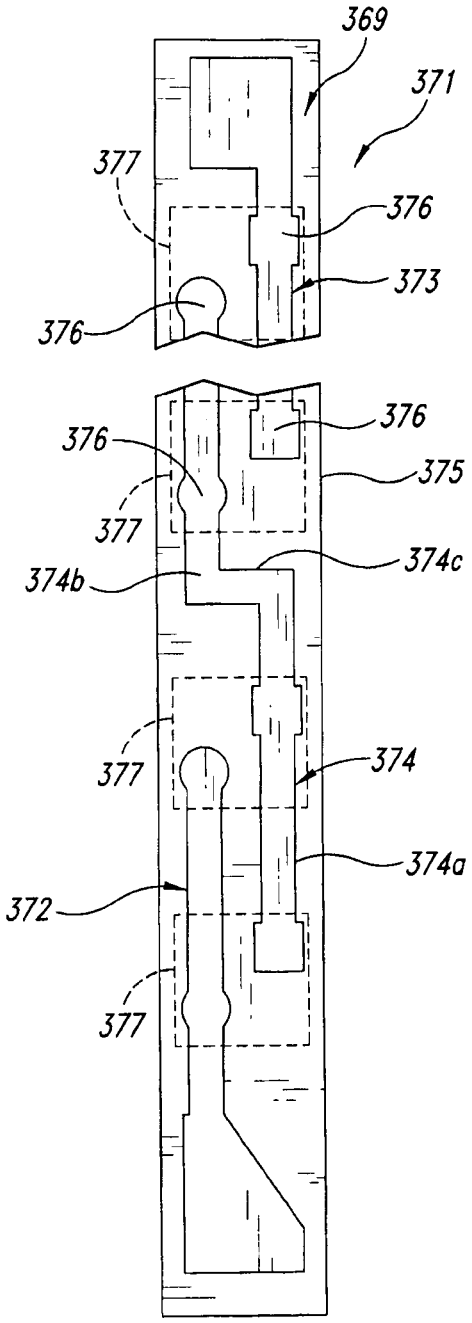
FIG. 14A is a top elevational view of a circuit having traces coupled to a base.

The light delivery systems described herein can have circuits with different configurations. The configurations of the circuits can be selected to achieve the desired output from each light source. FIGS. 14A to 16D illustrate circuits that can be used in the light delivery systems disclosed herein. FIG. 14A illustrates a circuit 371 including a trace system 369 having a plurality of traces 372, 373, 374 coupled to a base 375. Bonding pads 376 are positioned to receive the light sources 377 (shown in phantom).

At least one of the traces 372, 373, 374 can be a cross-over trace. In the illustrated embodiment of FIG. 14A, the trace 374 is a cross-over trace and includes a pair of opposing longitudinally-extending side portions 374A, 374B and a cross-over trace 374C extending laterally between the side portions 374A, 374B. In this manner, the trace 374 can connect opposing connectors of adjacent light sources 377. The circuit 371 can have any number of traces as desired.

Figure 14B:
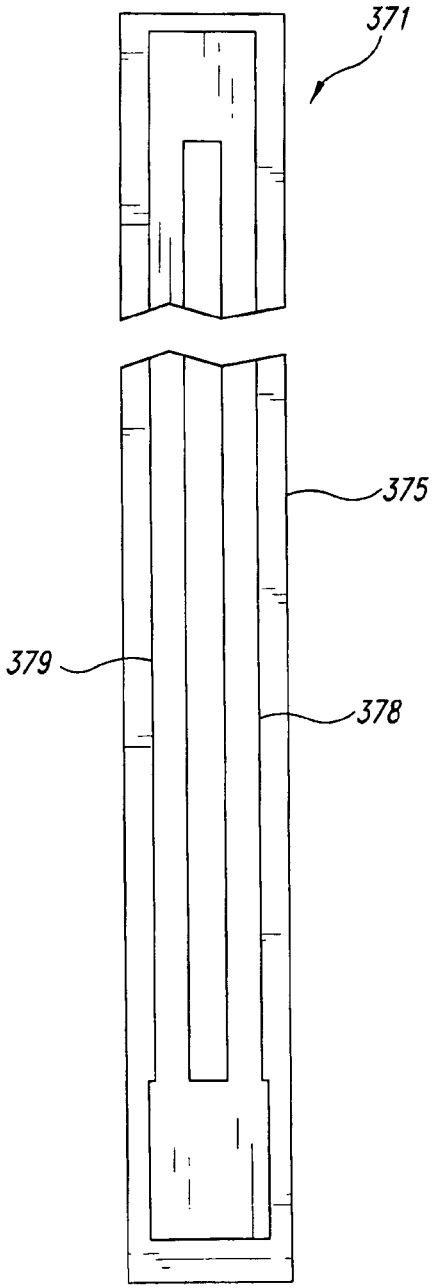
FIG. 14B is a bottom elevational view of the circuit of FIG. 14A.

A pair of return traces 378, 379 of FIG. 14B is coupled to the bottom surface of the base 375 and can increase the current carrying capability of the light delivery system without blocking a substantial amount of light emitted from the light sources 377. The return traces 378, 379 can be positioned directly opposite portions of the traces 372, 373, 374 such that the traces 378, 379 do not increase the amount of blocked light. In some embodiments, the width of the traces 378, 379 can be generally equal to or less than the width of the opposing portions of the corresponding traces 372, 373, 374.

Figure 15A:
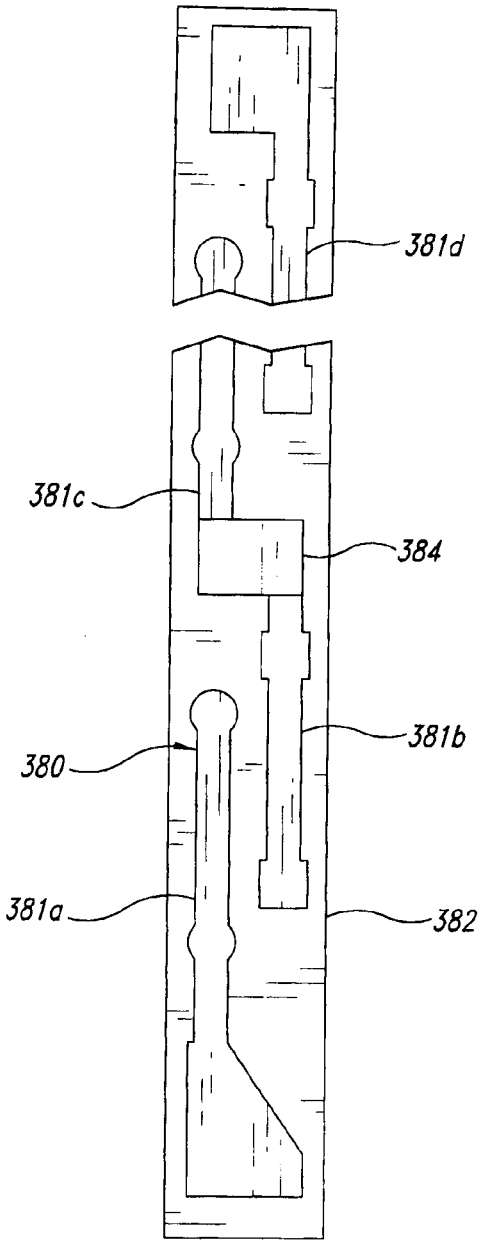
FIG. 15A is a top elevational view of circuit having traces coupled to a base, according to another illustrated embodiment.
Figure 15B:
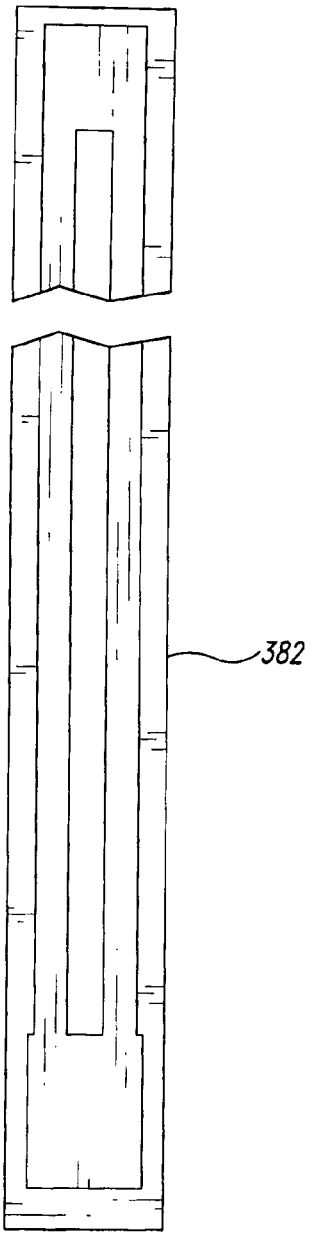
FIG. 15B is a bottom elevational view of the circuit of FIG. 15A.

FIGS. 15A and 15B illustrate another circuit for a light delivery system. A trace system 380 has segments that provide independent activation of one or more groups of light sources. The illustrated trace system 380 includes a plurality of traces 381A-D mounted to the base 382. A controller or switch 384 for selectively controlling current flow is positioned between the traces 381B, 381C. The controller 384 can thus determine the current flow to distal light sources (not shown). The illustrated trace system 380 has a single controller 384; however, any desired number of controllers can be used to separate one or more light sources.

Figure 16A:
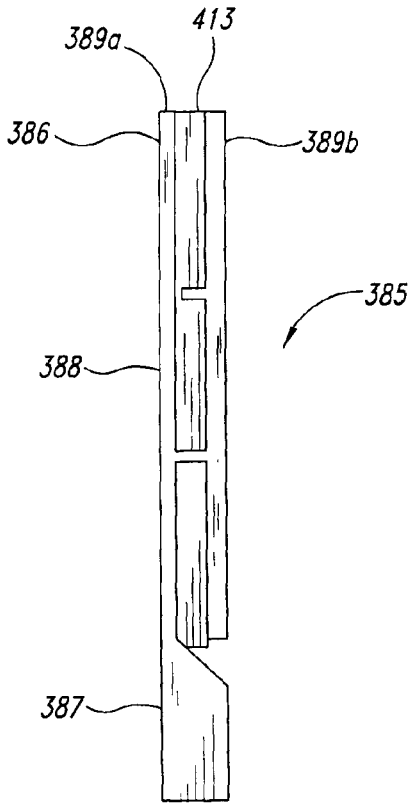
FIG. 16A is a top elevational view of a circuit having traces coupled to a base, in accordance with another illustrated embodiment.
Figure 16B:
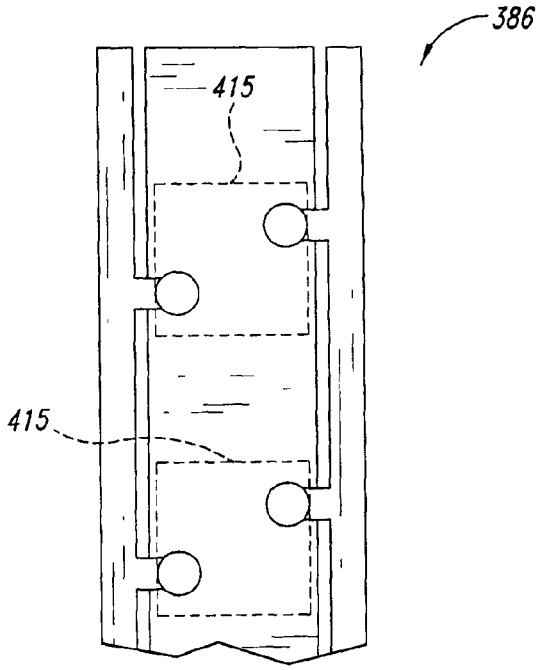
FIG. 16B is a distal portion of the circuit of FIG. 16A.
Figure 16C:
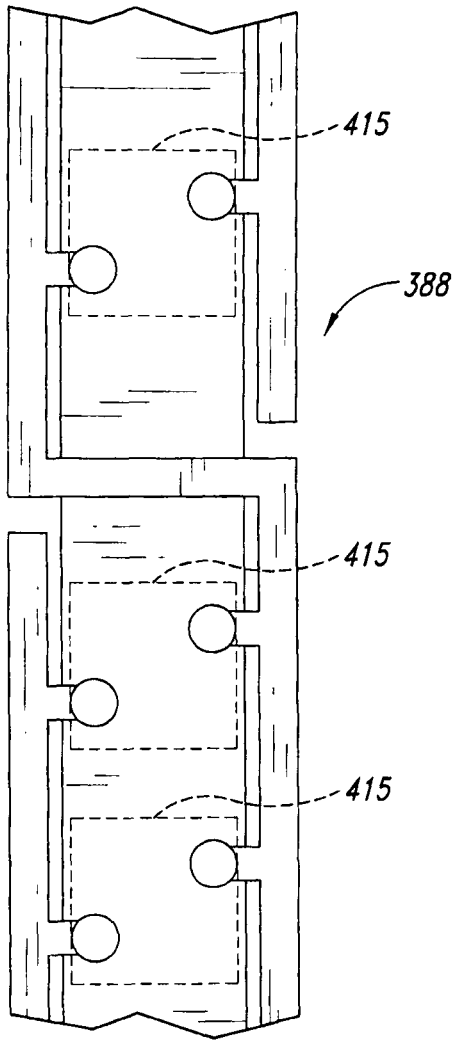
FIG. 16C is a central portion of the circuit of FIG. 16A.
Figure 16D:
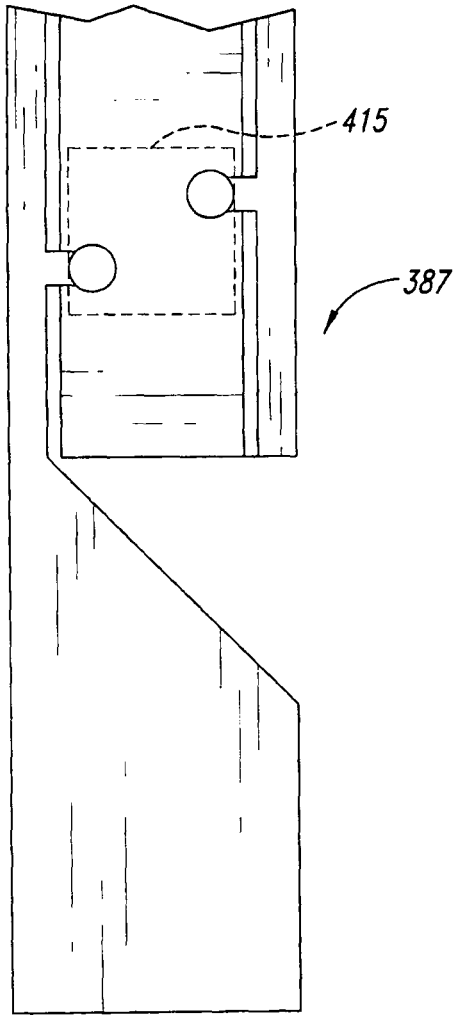
FIG. 16D is a proximal portion of the circuit of FIG. 16A.

FIGS. 16A to 16D show a light transmission system in accordance with one embodiment. The illustrated light transmission system 385 of FIG. 16A has a distal portion 386 (FIG. 16B), proximal portion 387 (FIG. 16D), and central portion 388 (FIG. 16C) extending therebetween. A pair of traces 389A, 389B extend along the length of the transmission system 385. A base 413 is positioned between the traces 389A, 389B. As shown in FIGS. 16B to 16D, light sources 415 (shown in phantom) can be spaced from each other along the light transmission system 385. The traces 389A, 389B are preferably spaced laterally from the light sources 415 for improved transmission through the base 413. In one embodiment, the base 413 is transparent.

The illustrated light transmission system 385 can have a single or double sided mounting arrangement. The material of the base 413 can be removed to improve the optical properties of the base 413. Laser and/or mechanical muting techniques can be used to remove a portion (e.g., a substantial portion) of the material of the base 413 positioned adjacent and/or beneath a plurality of light sources 415. Other types of material removal techniques, such as etching, can also be used.

Figure 17:
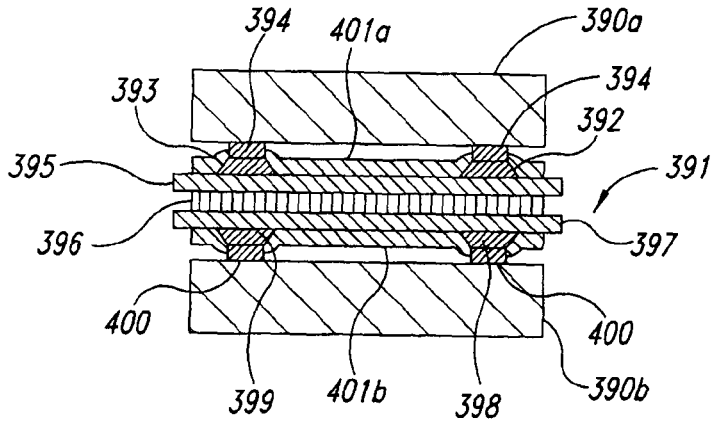
FIG. 17 is a cross-sectional view of a pair of light sources mounted to a multilayer circuit.

The circuits of FIGS. 14A to 16D can be used for a one-sided or two-sided flip chip mounting arrangement. FIG. 17 shows a two-sided arrangement having light sources 390A, 390B mounted to opposing sides of a multilayer board 391. The board 391 includes the light source 390A mounted to traces 392, 393 via solder 394. The traces 392, 393 are mounted to an upper surface of an upper base 395. A return trace 396 is interposed between the upper base 395 and a lower base 397. The light source 390B is mounted to traces 398, 399 via solder 400. Upper and lower coverlays 401A, 401B can cover and protect the traces 392, 393 and traces 398, 399, respectively. Of course, the board 391 can be transparent to allow the passage of light therethrough.

Figure 18A:
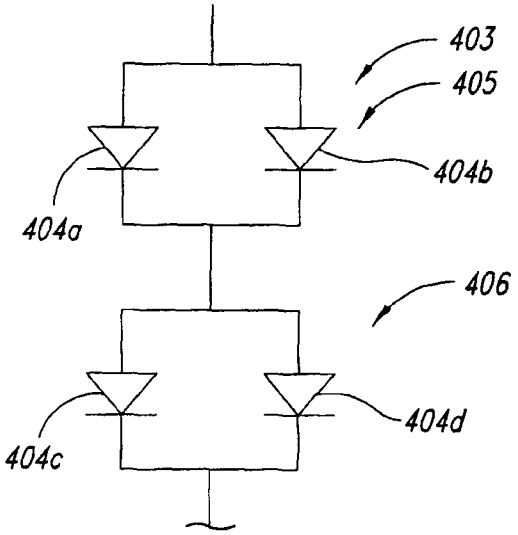
FIG. 18A is a circuit diagram of one embodiment of a light bar circuit.
Figure 18B:
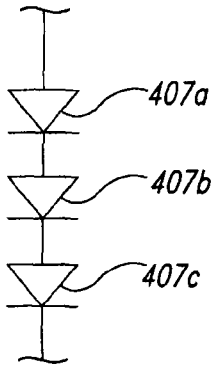
FIG. 18B is a circuit diagram of another embodiment of a light bar circuit.

As noted above, the light transmission systems disclosed herein can have various types of circuit arrangements. FIG. 18A is a circuit diagram 403 showing light sources 404A-D. The light sources 404A, 404B are in a parallel arrangement. The light sources 404C and 404D are likewise in a parallel arrangement. Any desired number of light sources can be arranged in a parallel arrangement. The light sources 404A, 404B and light sources 404C, 404D form groups 405, 406, respectively, that are arranged in series. Any number of light source groups can be arranged in series. FIG. 18B illustrates a plurality of light sources 407A-C in a series arrangement.

Figure 19:
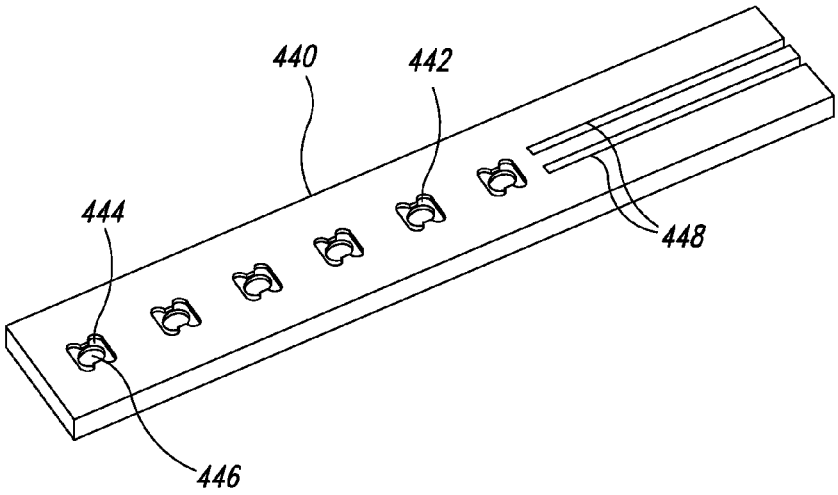
FIG. 19 is a perspective view of an empty manufacturing tool for holding the light sources of FIG. 11.
Figure 21:
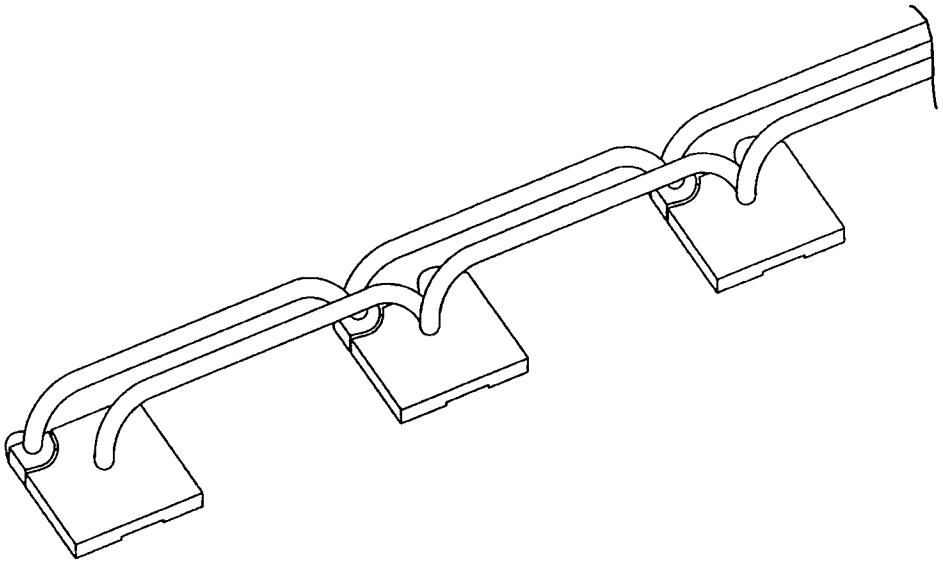
FIG. 21 is an enlarged perspective view of the light sources, wires, and manufacturing tool illustrated in FIG. 20.
Figure 23:
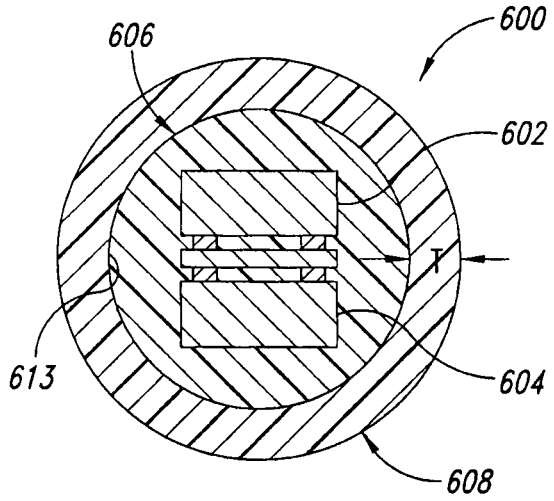
FIG. 23 is a schematic cross-sectional view of a distal tip having a two-sided light source array in accordance with another embodiment.

FIGS. 19 and 23 show methods of producing distal tips for light delivery systems. FIGS. 19 to 21 illustrate one embodiment of a process to produce a distal tip, such as the distal tip 400 of FIG. 11 as detailed below.

FIG. 19 shows a fixture device 440 that is configured to receive and hold the LEDs 410 during assembling. The illustrated fixture device 440 includes an array of holders 442 and a pair of elongated slots 448 extending along inwardly from one side of the fixture device 440. The holders 442 are sized and configured to receive at least a portion of the LEDs 410. The pattern of the holders 442 corresponds to the desired pattern of the LEDs. Each holder 442 comprises a mounting portion 444 and a through hole 446. The mounting portion 444 can be a recess configured to receive at least a portion of the LEDs. Alternatively, the mounting portions 444 can be one or more protrusions, keying structures, or other suitable structure for engaging and holding an LED.

In the illustrated embodiment, to place the LEDs 410 within a corresponding holder 442, the bottom portion of each LED 410 is placed within a corresponding mounting portion 444 such that the electrodes of the LED are facing outwardly, as shown in FIG. 20. To ensure that the LEDs are properly retained in their corresponding holders 442, a vacuum can be applied via the through hole 446. Optionally, the mounting portions 444 can have sealing members (e.g., rubber inserts, compliant flanges, etc.) to form a seal between the LEDs and holders 442. Preferably, the vacuum is continuously applied while wire leads are attached to the electrodes of the LEDs.

As shown in FIG. 20, wires extending from the outermost LED can pass through the slots 448 which function as wire holders. In this manner, the fixture device 440 can effectively hold the LEDs and wires in desired locations to ensure proper positioning and alignment. Once the light transmission system 450 is assembled (as shown in FIG. 20), the light transmission system 450 can be removed from the fixture device 440 for subsequent processing. If a vacuum was applied during assembling, the vacuum can be reduced or eliminated to permit easy removal of the LEDs from the fixture device 440. In some embodiments, a positive pressure is applied to release the LEDs from the tool. The assembled LEDs can then be place in a mold and encapsulated with material to the desired final dimensions, as discussed in connection with FIG. 23.

Figure 22:
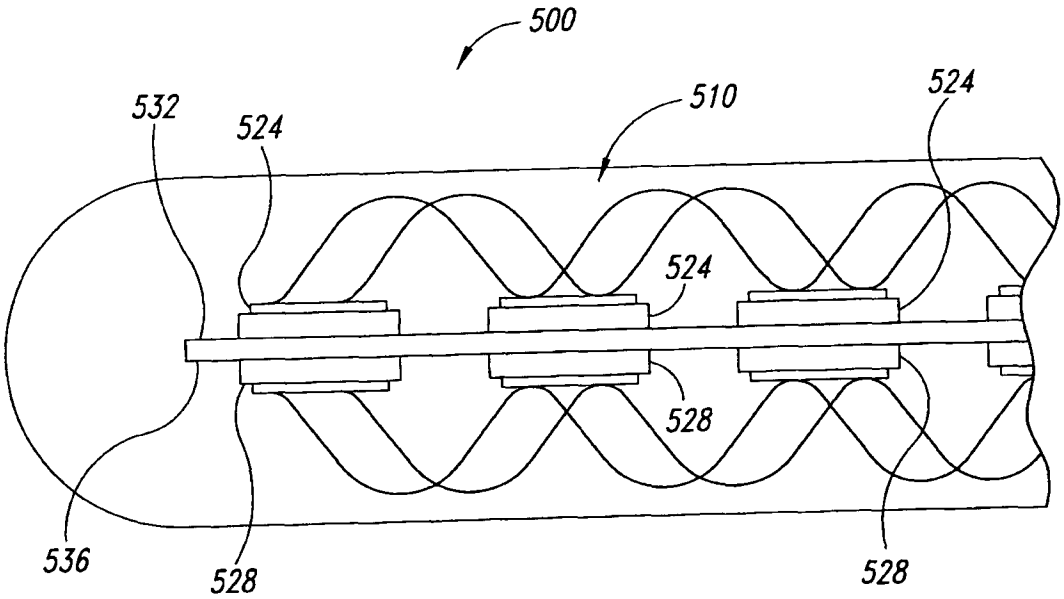
FIG. 22 is a side elevational schematic view of a distal tip having a two-sided light source array in accordance with one embodiment.

The distal tips described above can be modified to have light sources facing any number of directions. FIG. 22 shows a distal tip 500 having a two-sided light transmission system 510. The light transmission system 510 is interposed between a first array of light sources 524 and second array of light sources 528. In the illustrated embodiment, the wire bonded light sources 524, 528 are mounted to upper and lower faces 532, 536, respectively, of the base 510. The light sources 524, 528 can advantageously directly light in different directions, preferably in substantially opposite directions. The illustrated light sources 524, 528 can be applied to the base 510 by using the process illustrated in FIGS. 3A to 5B. In other embodiments, a two-sided light transmission system includes flip chip mounted light sources mounted to upper and lower faces of a base, preferably formed by the process illustrated in FIGS. 7 to 9. Thus, light sources can be applied to any number of faces of a mounting substrate.

FIG. 23 shows a distal portion of a light transmission system 600 having a two-side chip mounting arrangement. The light sources 602, 604 are encapsulated in an inner portion 606. An outer portion 608 is disposed over the inner portion 606.

The inner portion 606 can be formed through a casting or molding process, such as an injection molding process. The inner portion 606 and light sources 602, 604 can then be inserted into the outer portion 608. In one embodiment, the outer portion 608 is in the form of a tube. The outer portion 608 can be processed to bond, adhere, or otherwise couple the outer portion 608 to the inner portion 606. In some embodiments, the outer portion 608 is a thermoplastic elastomer tube (e.g., a polyether block amide tube, PEBAX® tube, etc.) that receives the inner portion 606. After assembling the inner and outer portions 606, 608, the assembly is heated to a reflow temperature to cause at least one of the inner portion 606 and outer portion 608 to flow, thereby coupling the inner and outer portions 606, 608. This reflow encapsulation process results in a strong bond formed between the inner and outer portions 606, 608.

In another embodiment, the light transmission system 600 is inserted into the outer portion 608. Material is injected into the lumen 613 of the outer portion 608 to form the inner portion 606. In some embodiments, molten polymer is injected into the lumen 613 and flows between the outer portion 608 and light transmission system 600. The polymer preferably fills the spaces with the lumen 613.

The thickness T of the outer portion 608 can be selected based on the desired overall axial width of the catheter. In the illustrated embodiment of FIG. 23, the inner portion 606 has a diameter in the range of about 0.015 inch (0.381 mm) to about 0.025 inch (0.635 mm). In some embodiments, the diameter of the inner portion 606 is about 0.020 inches (0.508 mm). The thickness T of the outer portion 608 can be in the range of about 0.002 inch (0.051 mm) to about 0.007 inch (0.178 mm). In some embodiments, the thickness T is about 0.005 inch (0.127 mm).

Generally, the light delivery systems can be positioned relative to a target site and then activated to deliver light to the target site. The light delivery systems can be used to treat organs, vasculature, tissue (e.g., epithelial tissue, connective tissue, muscle tissue and nerve tissue), and various systems including, but not limited to, organ systems, circulatory systems, and other suitable systems in the patient.

In some embodiments, the light delivery systems are used to treat adipose tissue, such as subcutaneous adipose tissue located directly beneath the skin or adipose tissue (e.g., visceral fat or intra-abdominal fat) located proximate internal organs. After administering a treatment agent, the light delivery systems can be used to remove or otherwise alter these types of adipose tissue. U.S. Patent Publication No. 2005-0085455, which is hereby incorporated by reference in its entirety, discloses various methods, treatment agents, and the like that can be used in combination with the light delivery systems described herein to treat visceral fat.

Visceral fat, such as panniculus adipose tissue, may have a contributory role in medical conditions, such as type II diabetes. The reduction of this visceral fat may improve a patient's condition. If a person is suffering from type II diabetes, for example, the reduction of visceral fat may reverse or improve insulin resistance, diabetes syndrome, and/or metabolic syndrome. This can lead to reduced medical costs associated with diabetes. The frequency and likelihood of complications (e.g., heart disease, renal failure, foot ulcers, and diabetic retinopathy, and the like) of diabetes can also be reduced or eliminated.

In some embodiments, the light delivery system 100 of FIG. 1 has the catheter assembly 110 dimensioned for insertion (e.g., percutaneous delivery) into and through a patient. The distal tip 114 can be moved into operative engagement with the patient's visceral fat. Once positioned, the distal tip 114 can illuminate the visceral fat for a desired period of time. In some non-limiting embodiments, for example, the catheter assembly 110 has an outer diameter less than about 1 mm for convenient placement within the patient.

Various delivery techniques can provide access to the visceral fat. A delivery device, such as an introducer or biopsy needle, can be used to access the visceral fat. The light delivery system 100 can be placed while utilizing a visualization technique (e.g., ultrasound, fluoroscopy, CT, and MRI) to facilitate proper positioning. One or more visualization aids can be provided on the system 100 to allow easy visualization in situ.

The treatment agent, such as talaporfin sodium, can be administered to the patient by a suitable delivery means. To deliver a therapeutically effective amount of the agent, the agent can be administered intravenously, or by any other suitable means. After the agent is adequately dispersed at the target site, the transmission system 120 is activated to illuminate the target site. For example, the transmission system 120 can be activated for about 1 hour and then removed from the patient. The transmission system 120 can be stopped automatically or by user input.

The treated adipose cells may break down (e.g., immediately or gradually over an extended period of time) and are subsequently absorbed by the patient's body. In this manner, the amount of visceral fat can be reduced in a controller manner. This procedure can be performed any number of times at different locations until the desired amount of fat has been eliminated. For example, visceral fat can be removed until achieving a noticeable improvement in insulin resistance. Of course, fat at other target sites can also be treated in a similar manner. Thus, fat deposits can be precisely destroyed or eliminated for health or cosmetic reasons. Moreover, because the system 100 has a low profile, the distal tip 114 can be delivered to remote locations using minimally invasive techniques.

The light delivery systems can also be dimensioned to fit within the vasculature system, such as within lumens of veins or arteries, or other anatomical lumens in the respiratory system, for example. The size of the light delivery system can be selected based the target treatment site and delivery path to the treatment site.

All of the above U.S. patents, U.S. patent application publications, U.S. patent applications, foreign patents, foreign patent applications and non-patent publications referred to in this specification and/or listed in the Application Data Sheet, to include U.S. Pat. Nos. 6,958,498; 6,784,460; 6,661,167; and 6,445,011; U.S. Publication No. 2005/0228260; International Patent Application Nos. PCT/US2005/032851 and PCT/US01/44046; and U.S. Provisional Patent Application No. 60/640,382 are incorporated herein by reference, in their entirety. Except as described herein, the embodiments, features, systems, devices, materials, methods and techniques described herein may, in some embodiments, be similar to any one or more of the embodiments, features, systems, devices, materials, methods and techniques described in the incorporated references. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned incorporated references.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. The materials, methods, ranges, and embodiments disclosed herein are given by way of example only and are not intended to limit the scope of the disclosure in any way. Accordingly, the invention is not intended to be limited by the specific disclosures of preferred embodiments disclosed herein.

What is claimed is:

1. A catheter assembly for performing light therapy on a subject, the assembly comprising:

a control system adapted to be operated by a user;

a catheter body extending from the control system, the catheter body dimensioned for placement within the subject; and a distal tip at an end of the catheter body, the distal tip including a transparent substrate having a plurality of locking features, wherein the transparent substrate is a substantially flat strip, wherein the entire flat strip comprises a transparent material, an array of spaced apart light sources for emitting light mounted on the flat strip and controlled by the control system, and a flexible outer member encapsulating both the substrate and the light sources, wherein portions of the flexible outer member pass through the locking features to lock the flexible outer member to the substrate, wherein the substantially flat strip carries a conductive connector adapted to provide power to the array of light sources and transmits most of the light emitted from the array of light sources towards the substrate such that a sufficient amount of light is transmitted through the substrate and the outer member to activate a therapeutically effective amount of treatment agent in the subject.

2. The catheter assembly of claim 1 wherein the outer member has a cross-sectional width that is less than about 1.25 mm.

3. The catheter assembly of claim 1 wherein the substrate has a substantially rectangular cross-sectional shape.

4. A [device] *kit* for performing a medical treatment, the [device] *kit* comprising:

*a photoreactive agent comprising talaporfin sodium;* a plurality of light sources capable of emitting light [for treating a patient] *to activate the photoreactive agent*;

a distal tip having a substantially flat strip and being dimensioned for placement within a patient, wherein the light sources are coupled to a section of the substantially flat strip, wherein substantially all of the section comprises a transmissive material such that a substantial portion of the light emitted from the plurality of light sources directed towards the strip is transmitted through the strip when the light sources are energized; and an outer member surrounding and encapsulating the strip and the plurality of light sources.

5. The [device] *kit* of claim 4 wherein the plurality of light sources is coupled to a flat surface of the strip.

6. The [device] *kit* of claim 4 wherein the outer member is dimensioned for percutaneous delivery to a target region within the patient.

7. The [device] *kit* of claim 4 wherein the outer member is made of plastic and encapsulates the strip and the plurality of light sources.

8. The [device] *kit* of claim 4 wherein the outer member has a cross-sectional width that is less than about 1.25 mm.

9. The [device] *kit* of claim 4 wherein the outer member has a cross-sectional width that is less than about 1 mm.

10. The [device] *kit* of claim 4 wherein the outer member has a cross-sectional width that is less than about 0.75 mm.

11. The [device] *kit* of claim 4 wherein one pair of leads electrically connects each adjacent pair of light sources.

12. The [device] *kit* of claim 4 wherein the plurality of light sources are LEDs mounted to the strip in a flip chip arrangement.

13. The [device] *kit* of claim 4 wherein the strip comprises a plurality of locking structures, at least one of the locking structures positioned between each adjacent pair of light sources.

14. The [device] *kit* of claim 13, wherein the outer member is an encapsulant surrounding the strip and light sources, wherein each locking structure is a through hole that receives a portion of the encapsulant.

15. The [device] *kit* of claim 4, further comprising:

means for electrically connecting the plurality of light sources.

16. The [device] *kit* of claim 15 wherein the means for electrically connecting the plurality of light sources comprises traces in communication with the light sources, the traces arranged to provide activation of a selected number of the light sources.

17. The [device] *kit* of claim 4 wherein the outer member physically contacts the plurality of light sources and the substrate.

18. The [device] *kit* of claim 4, further comprising a conductive connector that provides power to the plurality of light sources, the conductive connector being carried by the strip.

19. The [device] *kit* of claim 18 wherein the conductive connector and the light sources are directly connected to the strip.

20. The [device] *kit* of claim 4 wherein the light sources output light through portions of the distal tip on opposite sides of the strip.

21. The [device] *kit* of claim 4 wherein the light sources emit light in different direction such that light is emitted away from an upper face of the strip and an opposing lower face of the strip.

22. The [device] *kit* of claim 4, further comprising an optically transparent adhesive that couples the light sources to the section of the substantially flat, transparent support.

23. The [device] *kit* of claim 4, further comprising connectors that electrically connect the light sources together, wherein the connectors are spaced apart from the strip.

24. A method of producing a catheter for treating a patient, the method comprising:

coupling a plurality of light sources onto a substantially flat strip, the light sources being spaced from one another with respect to a longitudinal length of the substantially flat strip and mounted on a longitudinal section of the flat strip, wherein substantially all of the longitudinal section of the flat strip comprises a transparent material such that light from the light sources passes through the flat strip;

connecting the plurality of light sources to a power source for energizing the plurality of light sources; and placing an outer body around the flat strip and plurality of light sources coupled thereto, the outer body configured for positioning with a patient at a selected treatment location.

25. The method of claim 24 wherein the coupling of the plurality of light sources comprises mounting a series of LEDs upon the flat strip with a bonding material.

26. The method of claim 24 wherein the connecting of the plurality of light sources comprises connecting adjacent light sources with a pair of leads.

27. The method of claim 26 wherein each light source has a first side and an opposing second side, the first side is mounted to the flat strip and the leads are connected to the second side.

28. The method of claim 24 wherein the coupling of the plurality of light sources to the flat strip comprises:

coupling a pair of electrodes of each light source to a corresponding pair of mounting pads on the flat strip.

29. The method of claim 24, further comprising:

placing the light sources in an array of holders of a fixture device;

electrically coupling the light sources together while the light sources are retained in the holders;

after coupling the light sources together, removing the light sources from the fixture device.

30. The method of claim 29, further comprising applying a vacuum such that the light sources are pulled into corresponding holders.

31. A method of manufacturing a catheter for treating a patient, the method comprising:

placing a light transmission assembly in a lumen of an outer member, the light transmission assembly comprising a plurality of light sources coupled to a transparent flat section of a substantially flat strip positioned in the outer member, wherein the light sources are positioned to output light that travels through the transparent flat section of the flat strip; and after the light transmission assembly is in the outer member, thermally encapsulating the light transmission assembly in the outer member.

32. The method of claim 31 wherein the thermal encapsulation of the light transmission assembly includes melting the outer member onto the light transmission assembly.

33. The method of claim 31 wherein the thermal encapsulation of the light transmission assembly includes placing flowable material into the lumen of the outer member between the light transmission assembly and the outer member, and reflowing at least one of the flowable material and the outer member after placing the flowable material into the lumen of the outer member.

34. The method of claim 31 wherein the entire strip comprises an optically transparent material.

35. The method of claim 31 wherein the strip comprises windows positioned beneath the light sources.

36. A method of treating [visceral adipose] tissue, the method comprising:

*providing a photoreactive agent comprising talaporfin sodium to a patient;* providing a catheter having a distal end with a plurality of light sources, a substantially flat and transparent strip, and an outer member, wherein the distal end is sufficiently flexible for placement within [a] *the* patient, the light sources are carried by transparent material of the transparent strip, the transparent strip and the light sources are positioned within the outer member;

advancing the distal end of the catheter through the patient until the distal end is proximate to the [visceral adipose] tissue; and illuminating the [visceral adipose] tissue using the plurality of light sources such that light from the light sources travels through portions of the transparent strip carrying the light sources.

37. The method of claim 36 wherein illuminating the [visceral adipose] tissue with the plurality of light sources comprises activating [a treatment] *the photoreactive* agent in the [visceral adipose] tissue so as to destroy at least a portion of the [adipose] tissue.

38. A catheter for treating visceral adipose tissue, the catheter comprising:

a distal tip dimensioned for delivery through a patient, the distal tip being adapted to emit a sufficient amount of light to activate treatment agent in the visceral adipose tissue when the distal tip is in a treatment position, which is proximate to the adipose tissue, the distal tip including a cover, a substantially flat transparent strip carrying a conductive connector, a plurality of light sources coupled to a substantially flat and transparent section of the transparent strip such that the conductive connector delivers power to the plurality of light sources, the cover surrounding the light sources and the transparent section of the transparent strip, wherein substantially all of the transparent section of the transparent strip comprises a transparent material; and a main body extending from the distal tip, the main body dimensioned for percutaneous delivery of the distal tip to the treatment position.

39. The catheter of claim 38 wherein the energized distal tip emits sufficient amount of light to activate treatment agent in the visceral adipose tissue to destroy the visceral adipose tissue illuminated by the distal tip.

40. A method of manufacturing a catheter for treating a patient, the method comprising:

coupling a plurality of light sources to a portion of a substantially flat transmissive strip, the entire portion of the strip carrying the light sources comprises a transmissive material;

electrically coupling together the plurality of light sources using a conductive connector coupled to the portion of the strip such that a power source can energize the plurality of light sources; and forming an outer body about the strip and plurality of light sources coupled thereto, the strip of transmissive material extending longitudinally along the outer body and between the plurality of light sources, the outer body dimensioned for placement within a patient.

41. The method of claim 40 wherein electrically coupling together the plurality of light sources comprises connecting adjacent light sources with a pair of leads of the conductive connector.

42. The method of claim 40, further comprising:

coupling a power source to the plurality of light sources, the power source capable of simultaneously energizing a substantial number of the light sources.

43. A [device] *kit* for performing a medical treatment, the device comprising:

*a photoreactive agent comprising talaporfin sodium;* a plurality of light sources capable of emitting light [for treating a patient] *to activate the photoreactive agent*;

a substantially flat and transparent support made of a transmissive material, the support carrying the plurality of light sources such that light emitted from the plurality of light sources directed towards the support is transmitted through portions of the support carrying the light sources when the light sources are energized; and an outer member dimensioned for placement in [the] *a* patient and encapsulating the plurality of light sources and the support, the plurality of light sources physically contacting and being embedded in the outer member.

44. The [device] *kit* of claim 43 wherein at least one of the light sources extends across most of a width of the transparent support.

45. The [device] *kit* of claim 43, further comprising an optically transparent adhesive that couples the light sources to the support.

* * * * *